(12) United States Patent
Kinoshita et al.

(10) Patent No.: US 8,710,235 B2
(45) Date of Patent: *Apr. 29, 2014

(54) ORGANIC ELECTROLUMINESCENCE DEVICE

(75) Inventors: Ikuo Kinoshita, Kanagawa (JP); Kazunari Yagi, Kanagawa (JP); Takeshi Murakami, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/587,201

(22) Filed: Aug. 16, 2012

(65) Prior Publication Data

US 2012/0309980 A1 Dec. 6, 2012

Related U.S. Application Data

(62) Division of application No. 12/236,695, filed on Sep. 24, 2008, now Pat. No. 8,263,236.

(30) Foreign Application Priority Data

Sep. 25, 2007 (JP) .................................. 2007-247494

(51) Int. Cl.
*C09K 11/06* (2006.01)
*H01L 51/54* (2006.01)

(52) U.S. Cl.
USPC ..... 548/103; 428/917; 313/504; 257/E51.044

(58) Field of Classification Search
None
See application file for complete search history.

(56) References Cited

U.S. PATENT DOCUMENTS

| | | | |
|---|---|---|---|
| 6,303,238 B1 | 10/2001 | Thompson et al. | |
| 7,771,845 B2 | 8/2010 | Sano et al. | |
| 8,263,236 B2 * | 9/2012 | Kinoshita et al. | 428/690 |
| 2004/0253478 A1 | 12/2004 | Thompson et al. | |
| 2006/0204787 A1 | 9/2006 | Sano et al. | |
| 2007/0082284 A1 | 4/2007 | Stoessel et al. | |
| 2008/0036373 A1 | 2/2008 | Itoh et al. | |

FOREIGN PATENT DOCUMENTS

| | | |
|---|---|---|
| EP | 1 647 554 A2 | 4/2006 |
| JP | 2006-232784 A | 9/2006 |
| JP | 2007-096255 A | 4/2007 |
| WO | 00/57676 A1 | 9/2000 |
| WO | 2008/117889 A1 | 10/2008 |

OTHER PUBLICATIONS

Extended European Search Report dated Dec. 11, 2008 for EP Application No. 08016773.7.

* cited by examiner

*Primary Examiner* — Marie R. Yamnitzky
(74) *Attorney, Agent, or Firm* — Morgan Lewis & Bockius LLP

(57) ABSTRACT

A compound is represented by the following formula (I):

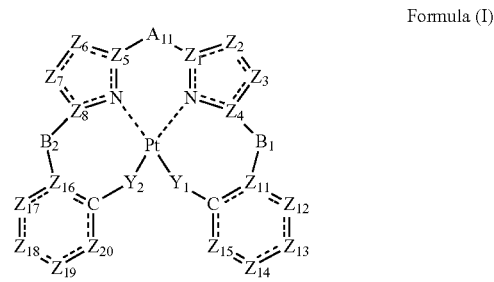

Formula (I)

wherein N represents a nitrogen atom; C represents a carbon atom; Pt represents a platinum atom; $Z_1$, $Z_4$, $Z_5$, and $Z_8$ represent a carbon atom or a nitrogen atom; $Z_2$, $Z_3$, $Z_6$, and $Z_7$ represent a carbon atom, a nitrogen atom, an oxygen atom or a sulfur atom; $Z_{11}$ and $Z_{16}$ represent a carbon atom or a nitrogen atom; $Z_{12}$, $Z_{13}$, $Z_{14}$, $Z_{15}$, $Z_{17}$, $Z_{18}$, $Z_{19}$, and $Z_{20}$ represent a carbon atom, a nitrogen atom, an oxygen atom, or a sulfur atom; $Y_1$ and $Y_2$ represent a single bond, an oxygen atom, a sulfur atom, a nitrogen atom; $A_{11}$ represents a divalent linking group; $B_1$ and $B_2$ represent a single bond or a divalent linking group.

1 Claim, No Drawings

ORGANIC ELECTROLUMINESCENCE DEVICE

This application is a divisional of U.S. application Ser. No. 12/236,695, filed Sep. 24, 2008, now U.S. Pat. No. 8,263,236, which claims priority to JP 2007-247494, filed Sep. 25, 2007, each of which is incorporated herein by reference in its entirety.

BACKGROUND OF THE INVENTION

1. Field of the Invention

The present invention relates to a metal complex compound and an organic electroluminescence device containing the compound.

2. Description of the Related Art

Since organic electroluminescence devices (organic EL devices) can provide light emission having high luminance even at a low driving voltage, active research and development on them have been made in recent years. In general, organic EL devices have organic layers including a light emitting layer and a pair of electrodes sandwiching these layers therebetween. Electrons injected from a cathode and holes injected from an anode recombine in the light emitting layer and energy of excitons thus generated is utilized for light emission.

Use of a phosphorescent material has recently accelerated improvement in the efficiency of the device. Iridium complexes and platinum complexes are known as the phosphorescent material (refer to, for example, U.S. Pat. No. 6,303,238 and International Patent Publication No. 00/57676), but development of devices satisfying both high efficiency and high durability has not yet led to success. There is therefore an eager demand for the development of a phosphorescent material capable of satisfying both of them.

There are disclosed organic electroluminescence devices containing, in a light emitting layer thereof, a material of a phenylpyrazole tetradentate platinum complex (for example, JP-A-2006-232784 and JP-A-2007-96255). These devices are however insufficient from the viewpoint of luminescence quantum efficiency, driving voltage, consumption power, and durability and are required to be improved further by specifying the structure of the platinum complex. In particular, they are required to have improved luminescence quantum efficiency, driving voltage, consumption power, and durability in phosphorescence emission of a blue to bluish green light which is a shorter wavelength light.

SUMMARY OF THE INVENTION

An object of the present invention is to provide a metal complex compound having good light emission properties (emission wavelength, luminance, quantum yield, and driving voltage) and durability; and an organic electroluminescence device containing the compound.

The problem has been overcome by the following means:
(1) A compound represented by the following formula (I):

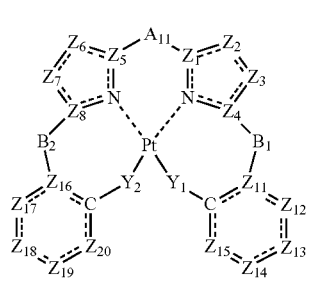

Formula (I)

wherein
N represents a nitrogen atom,
C represents a carbon atom,
Pt represents a platinum atom,
each of $Z_1$, $Z_4$, $Z_5$, and $Z_8$ independently represents a substituted or unsubstituted carbon atom or a nitrogen atom,
each of $Z_2$, $Z_3$, $Z_6$, and $Z_7$ independently represents a substituted or unsubstituted carbon atom, a substituted or unsubstituted nitrogen atom, an oxygen atom or a sulfur atom,
each bond between atoms of a 5-membered ring formed by $Z_1$, $Z_2$, $Z_3$, $Z_4$, and a nitrogen atom represents a single bond or a double bond,
each bond between atoms of a 5-membered ring formed by $Z_5$, $Z_6$, $Z_7$, $Z_8$, and a nitrogen atom represents a single bond or a double bond,
when $Z_1$, $Z_2$, $Z_3$, $Z_4$, $Z_5$, $Z_6$, $Z_7$, and $Z_8$ can have a substituent, the substituent is selected from the following Substituent Group A,
each of $Z_{11}$ and $Z_{16}$ independently represents a substituted or unsubstituted carbon atom or a nitrogen atom,
each of $Z_{12}$, $Z_{13}$, $Z_{14}$, $Z_{15}$, $Z_{17}$, $Z_{18}$, $Z_{19}$, and $Z_{20}$ independently represents an atom selected from a substituted or unsubstituted carbon atom, a substituted or unsubstituted nitrogen atom, an oxygen atom, and a sulfur atom,
$Z_{12}$ and $Z_{13}$, $Z_{13}$ and $Z_{14}$, $Z_{17}$ and $Z_{18}$, or $Z_{18}$ and $Z_{19}$ may be coupled together via a substituent to form a fused ring structure, at least one pair selected from the pairs of $Z_{12}$ and $Z_{13}$, $Z_{13}$ and $Z_{14}$, $Z_{17}$ and $Z_{18}$, and $Z_{18}$ and $Z_{19}$ forms a 5-membered ring via a substituent,
when $Z_{12}$ and $Z_{13}$, $Z_{13}$ and $Z_{14}$, $Z_{17}$ and $Z_{18}$, or $Z_{18}$ and $Z_{19}$ form a 5-membered ring via a substituent, the 5-membered ring may have another fused ring structure,
each bond between atoms of a 6-membered ring formed by $Z_{11}$, $Z_{12}$, $Z_{13}$, $Z_{14}$, $Z_{15}$ and a carbon atom represents a single bond or a double bond,
each bond between atoms of a 6-membered ring formed by $Z_{16}$, $Z_{17}$, $Z_{18}$, $Z_{19}$, $Z_{20}$, and a carbon atom represents a single bond or a double bond,
when $Z_{11}$, $Z_{12}$, $Z_{13}$, $Z_{14}$, $Z_{15}$, $Z_{16}$, $Z_{17}$, $Z_{18}$, $Z_{19}$, and $Z_{20}$ can have a substituent, the substituent is selected from the Substituent group A,
each of $Y_1$ and $Y_2$ independently represents a single bond, an oxygen atom, a sulfur atom, a nitrogen atom which may have a substituent selected from the Substituent group A, or an unsubstituted nitrogen atom,
$A_{11}$ represents a divalent linking group, and
each of $B_1$ and $B_2$ independently represents a single bond or a divalent linking group,
wherein
the Substituent group A consists of an alkyl group, a cycloalkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amide group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group, a silyl group, and a silyloxy group.

(2) The compound as described in above (1),
wherein the formula (I) is represented by the following formula (II) or (III):

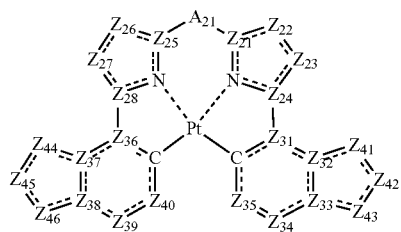

Formula (II)

wherein,
N represents a nitrogen atom,
C represents a carbon atom,
Pt represents a platinum atom;
each of $Z_{21}$, $Z_{24}$, $Z_{25}$, and $Z_{28}$ independently represents a substituted or unsubstituted carbon atom or a nitrogen atom,
each of $Z_{22}$, $Z_{23}$, $Z_{26}$, and $Z_{27}$ independently represents a substituted or unsubstituted carbon atom, a substituted or unsubstituted nitrogen atom, an oxygen atom, or a sulfur atom,
each bond between atoms of a 5-membered ring formed by $Z_{21}$, $Z_{22}$, $Z_{23}$, $Z_{24}$, and a nitrogen atom represents a single bond or a double bond,
each bond between atoms of a 5-membered ring formed by $Z_{25}$, $Z_{26}$, $Z_{27}$, $Z_{28}$, and a nitrogen atom represents a single bond or a double bond,
when $Z_{21}$, $Z_{22}$, $Z_{23}$, $Z_{24}$, $Z_{25}$, $Z_{26}$, $Z_{27}$, and $Z_{28}$ can have a substituent, each thereof may independently have a substituent selected from the Substituent Group A,
each of $Z_{34}$, $Z_{35}$, $Z_{39}$, and $Z_{40}$ independently represents a substituted or unsubstituted carbon atom, a substituted or unsubstituted nitrogen atom, an oxygen atom, or a sulfur atom,
each of $Z_{41}$, $Z_{42}$, $Z_{43}$, $Z_{44}$, $Z_{45}$ and $Z_{46}$ independently represents a substituted or unsubstituted carbon atom, a substituted or unsubstituted nitrogen atom, an oxygen atom, a sulfur atom, a selenium atom, or a tellurium atom,
each of $Z_{31}$, $Z_{32}$, $Z_{33}$, $Z_{36}$, $Z_{37}$, and $Z_{38}$ independently represents a substituted or unsubstituted carbon atom or a nitrogen atom,
each bond between atoms of a (6-membered+5-membered) fused ring formed by $Z_{31}$, $Z_{32}$, $Z_{33}$, $Z_{34}$, $Z_{35}$, $Z_{41}$, $Z_{42}$, $Z_{43}$ and a carbon atom represents a single bond or a double bond
each bond between atoms of a (6-membered+5-membered) fused ring formed by $Z_{36}$, $Z_{37}$, $Z_{38}$, $Z_{39}$, $Z_{40}$, $Z_{44}$, $Z_{45}$, $Z_{46}$, and a carbon atom represents a single bond or a double bond, $Z_{41}$ and $Z_{42}$, $Z_{42}$ and $Z_{43}$, $Z_{44}$ and $Z_{45}$, or $Z_{45}$ and $Z_{46}$ may be coupled together to form a ring,
when $Z_{31}$, $Z_{32}$, $Z_{33}$, $Z_{34}$, $Z_{35}$, $Z_{36}$, $Z_{37}$, $Z_{38}$, $Z_{39}$, $Z_{40}$, $Z_{41}$, $Z_{42}$, $Z_{43}$, $Z_{44}$, $Z_{45}$, and $Z_{46}$ can have a substituent, each thereof may independently have a substituent selected from the Substituent group A, and
$A_{21}$ represents a divalent linking group,

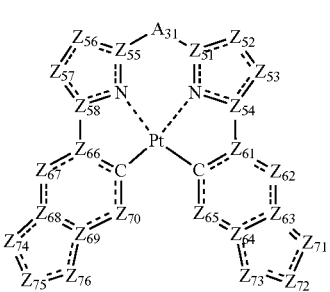

Formula (III)

wherein
N represents a nitrogen atom,
C represents a carbon atom,
Pt represents a platinum atom;
each of $Z_{51}$, $Z_{54}$, $Z_{55}$, and $Z_{58}$ independently represents a substituted or unsubstituted carbon atom or a nitrogen atom,
each of $Z_{52}$, $Z_{53}$, $Z_{56}$, and $Z_{57}$ independently represents a substituted or unsubstituted carbon atom, a substituted or unsubstituted nitrogen atom, an oxygen atom, or a sulfur atom,
each bond between atoms of a 5-membered ring formed by $Z_{51}$, $Z_{52}$, $Z_{53}$, $Z_{54}$, and a nitrogen atom represents a single bond or a double bond,
each bond between atoms of a 5-membered ring formed by $Z_{55}$, $Z_{56}$, $Z_{57}$, $Z_{58}$, and a nitrogen atom represents a single bond or a double bond,
when $Z_{51}$, $Z_{52}$, $Z_{53}$, $Z_{54}$, $Z_{55}$, $Z_{56}$, $Z_{57}$, and $Z_{58}$ can have a substituent, each thereof may independently have a substituent selected from the Substituent group A,
each of $Z_{62}$, $Z_{65}$, $Z_{67}$, and $Z_{70}$ independently represents a substituted or unsubstituted carbon atom, a substituted or unsubstituted nitrogen atom, an oxygen atom, or a sulfur atom;
each of $Z_{71}$, $Z_{72}$, $Z_{73}$, $Z_{74}$, $Z_{75}$ and $Z_{76}$ independently represents a substituted or unsubstituted carbon atom, a substituted or unsubstituted nitrogen atom, an oxygen atom, a sulfur atom, a selenium atom, or a tellurium atom,
each of $Z_{61}$, $Z_{63}$, $Z_{64}$, $Z_{66}$, $Z_{68}$, and $Z_{69}$ independently represents a substituted or unsubstituted carbon atom or a nitrogen atom,
each bond between atoms of a (6-membered+5-membered) fused ring formed by $Z_{61}$, $Z_{62}$, $Z_{63}$, $Z_{64}$, $Z_{65}$, $Z_{71}$, $Z_{72}$, $Z_{73}$, and a carbon atom represents a single bond or a double bond,
each bond between atoms of a (6-membered+5-membered) fused ring formed by $Z_{66}$, $Z_{67}$, $Z_{68}$, $Z_{69}$, $Z_{70}$, $Z_{74}$, $Z_{75}$, $Z_{76}$, and a carbon atom represents a single bond or a double bond,
$Z_{71}$ and $Z_{72}$, $Z_{72}$ and $Z_{73}$, $Z_{74}$ and $Z_{75}$, or $Z_{75}$ and $Z_{76}$ may be coupled together to form a ring, when $Z_{61}, Z_{62}, Z_{63}, Z_{64}, Z_{65}, Z_{66}, Z_{67}, Z_{68}, Z_{69}, Z_{70}, Z_{71}, Z_{72}, Z_{73}, Z_{74}, Z_{75}$, and $Z_{76}$ can have a substituent, each thereof may independently have a substituent selected from the Substituent group A, and $A_{31}$ represents a divalent linking group.

(3) The compound as described in above (2), wherein the formula (II) or (III) is represented by the following formula (IV) or (V), respectively:

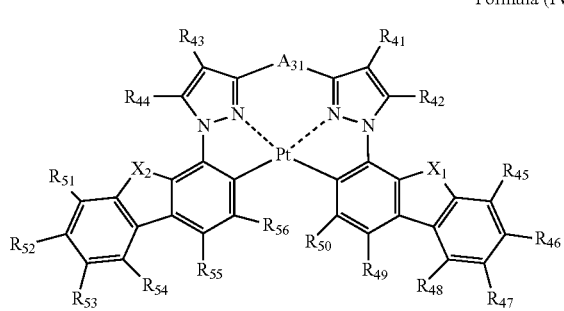

Formula (IV)

wherein each of $X_1$ and $X_2$ independently represents a substituted or unsubstituted carbon atom, a substituted or unsubstituted nitrogen atom, an oxygen atom, a sulfur atom, or a selenium atom, each of $R_{41}, R_{42}, R_{43}, R_{44}, R_{45}, R_{46}, R_{47}, R_{48}, R_{49}, R_{50}, R_{51}, R_{52}, R_{53}, R_{54}, R_{55}$, and $R_{56}$ independently represents a hydrogen atom or a substituent selected from the Substituent group A, and $A_{41}$ represents a divalent linking group,

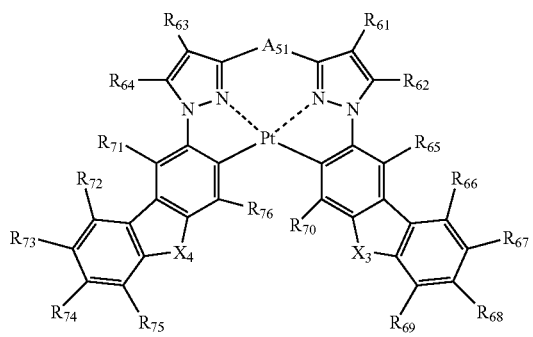

Formula (V)

wherein each of $X_3$ and $X_4$ independently represents a substituted or unsubstituted carbon atom, a substituted or unsubstituted nitrogen atom, an oxygen atom, a sulfur atom or a selenium atom, each of $R_{61}, R_{62}, R_{63}, R_{64}, R_{65}, R_{66}, R_{67}, R_{68}, R_{69}, R_{70}, R_{71}, R_{72}, R_{73}, R_{74}, R_{75}$, and $R_{76}$ independently represents a hydrogen atom or a substituent selected from the Substituent group A, and $A_{51}$ represents a divalent linking group.

(4) The compound as described in any one of above (1) to (3), wherein in the formulas (I) to (V), each of $A_{11}, A_{21}, A_{31}, A_{41}$, and $A_{51}$ independently represents a group selected from —C($R_{81}$)($R_{82}$)—, —C($R_{83}$)($R_{84}$)C($R_{85}$)($R_{86}$)—, —Si($R_{87}$)($R_{88}$)—, —N($R_{89}$)—, —O—, —S—, —SO—, —SO$_2$—, or —CO—, wherein each of $R_{81}, R_{82}, R_{83}, R_{84}, R_{85}, R_{86}, R_{87}, R_{88}$, and $R_{89}$ independently represents a hydrogen atom or a substituent selected from the Substituent group A.

(5) The compound as described in (3), wherein the formula (IV) or (V) is represented by the following formula (VI) or (VII), respectively:

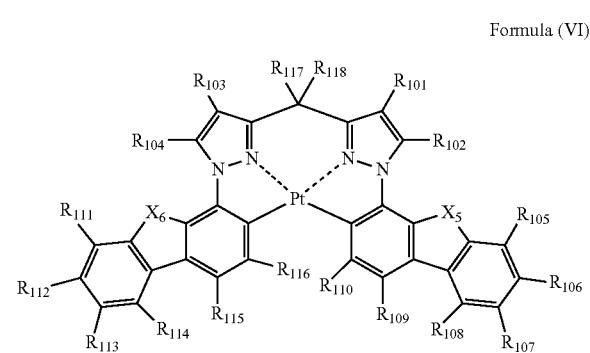

Formula (VI)

wherein each of $X_5$ and $X_6$ independently represents an oxygen atom or a sulfur atom, each of $R_{101}, R_{102}, R_{103}, R_{104}, R_{105}, R_{106}, R_{107}, R_{108}, R_{109}, R_{110}, R_{111}, R_{112}, R_{113}, R_{114}, R_{115}$ and $R_{116}$ independently represents a hydrogen atom or a substituent selected from the Substituent group A, and $R_{117}$ and $R_{118}$ represent alkyl groups, cycloalkyl groups or aryl groups, Formula (VII)

wherein each of $X_7$ and $X_8$ independently represents an oxygen atom or a sulfur atom, each of $R_{121}, R_{122}, R_{123}, R_{124}, R_{125}, R_{126}, R_{127}, R_{128}, R_{129}, R_{130}, R_{111}, R_{112}, R_{133}, R_{134}, R_{135}$ and $R_{136}$ independently represents a hydrogen atom or a substituent selected from the Substituent group A, and $R_{137}$ and $R_{138}$ represent alkyl groups, cycloalkyl groups or aryl groups.

(6) An organic electroluminescence device comprising:

a pair of electrodes; and an organic layer between the pair of electrodes, which contains the compound as described in above (1).

(7) An organic electroluminescence device comprising:
a pair of electrodes; and
an organic layer between the pair of electrodes, which comprises a light emitting layer that contains
the compound as described in above (1), and
a host material having a lowest excited triplet energy level ($T_1$ level), in the form of a single layer, of 61 kcal/mol or greater.

DETAILED DESCRIPTION OF THE INVENTION

The compound according to an embodiment of the invention is represented by the following formula (I).

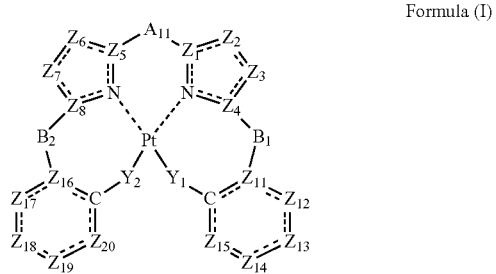

Formula (I)

In the formula (I), N represents a nitrogen atom, C represents a carbon atom, and Pt represents a platinum atom. Each of $Z_1$, $Z_4$, $Z_5$ and $Z_8$ independently represents a substituted or unsubstituted carbon atom, or a nitrogen atom; and each of $Z_2$, $Z_3$, $Z_6$ and $Z_7$ independently represents a substituted or unsubstituted carbon atom, a substituted or unsubstituted nitrogen atom, an oxygen atom, or a sulfur atom. The bond between each pair of adjacent atoms in the 5-membered rings, one of which is formed of $Z_1$, $Z_2$, $Z_3$, $Z_4$ and the nitrogen atom, and the other of which is formed of $Z_5$, $Z_6$, $Z_7$, $Z_8$ and the nitrogen atom, represents a single bond, or a double bond. When each of $Z_1$, $Z_2$, $Z_3$, $Z_4$, $Z_5$, $Z_6$, $Z_7$ and $Z_8$ can have a substituent, the substituent represents a substituent selected from Substituent group A. Each of $Z_{11}$ and $Z_{16}$ independently represents a substituted or unsubstituted carbon atom, or a nitrogen atom; and each of $Z_{12}$, $Z_{13}$, $Z_{14}$, $Z_{15}$, $Z_{17}$, $Z_{18}$, $Z_{19}$ and $Z_{20}$ independently represents an atom selected from a substituted or unsubstituted carbon atom, a substituted or unsubstituted nitrogen atom, an oxygen atom or a sulfur atom. $Z_{12}$ and $Z_{13}$, $Z_{13}$ and $Z_{14}$, $Z_{17}$ and $Z_{18}$, or $Z_{18}$ and $Z_{19}$ may be linked together via their substituents to form a fused ring structure, and at least one combination selected from four combinations, $Z_{12}$ and $Z_{13}$, $Z_{13}$ and $Z_{14}$, $Z_{17}$ and $Z_{18}$, or $Z_{18}$ and $Z_{19}$, forms a 5-membered ring via its substituents. When the combination of $Z_{12}$ and $Z_{13}$, $Z_{13}$ and $Z_{14}$, $Z_{17}$ and $Z_{18}$, or $Z_{18}$ and $Z_{19}$ forms a 5-membered ring via its substituents, the 5-membered ring formed may have a further fused-ring structure. The bond between each pair of adjacent atoms in the 6-membered rings, one of which is formed of $Z_{11}$, $Z_{12}$, $Z_{13}$, $Z_{14}$, $Z_{15}$ and the carbon atom, and the other of which is formed of $Z_{16}$, $Z_{17}$, $Z_{18}$, $Z_{19}$, $Z_{20}$ and the carbon atom, represents a single bond, or a double bond. When each of $Z_{11}$, $Z_{12}$, $Z_{13}$, $Z_{14}$, $Z_{15}$, $Z_{16}$, $Z_{17}$, $Z_{18}$, $Z_{19}$ and $Z_{20}$ can have a substituent, the substituent is a substituent selected from Substituent group A. Each of $Y_1$ and $Y_2$ independently represents a single bond, an oxygen atom, a sulfur atom, a nitrogen atom having a substituent selected individually from Substituent group A, or an unsubstituted nitrogen atom. $A_{11}$ represents a divalent linking group. Each of $B_1$ and $B_2$ independently represents a single bond, or a divalent linking group.

The term "Substituent group A" as used herein is defined as follows.

(Substituent Group A)

Substituent group A includes alkyl groups (preferably $C_{1-30}$, more preferably $C_{1-20}$, especially preferably $C_{1-10}$ alkyl groups such as methyl, ethyl, isopropyl, tert-butyl, n-octyl, n-decyl, and n-hexadecyl), cycloalkyl groups (preferably $C_{3-30}$, more preferably $C_{1-20}$, especially preferably $C_{3-10}$ alkyl groups such as cyclopropyl, cyclopentyl, and cyclohexyl), alkenyl groups (preferably $C_{2-30}$, more preferably $C_{2-20}$, especially preferably $C_{2-10}$ alkenyl groups such as vinyl, allyl, 2-butenyl, and 3-pentenyl), alkynyl groups (preferably $C_{2-30}$, more preferably $C_{2-20}$, especially preferably $C_{2-10}$ alkynyl groups such as propargyl and 3-pentynyl), aryl groups (preferably $C_{6-30}$, more preferably $C_{6-20}$, especially preferably $C_{6-12}$ aryl groups such as phenyl, p-methylphenyl, naphthyl, and anthranyl), amino groups (preferably $C_{0-30}$, more preferably $C_{0-20}$, especially preferably $C_{0-10}$ amino groups such as amino, methylamino, dimethylamino, diethylamino, dibenzylamino, diphenylamino, and ditolylamino), alkoxy groups (preferably $C_{1-30}$, more preferably $C_{1-20}$, especially preferably $C_{1-10}$-alkoxy groups such as methoxy, ethoxy, butoxy, and 2-ethylhexyloxy), aryloxy groups (preferably $C_{6-30}$, more preferably $C_{6-20}$, especially preferably $C_{6-12}$ aryloxy groups such as phenyloxy, 1-naphthyloxy, and 2-naphthyloxy), heterocyclic oxy groups (preferably $C_{1-30}$, more preferably $C_{1-20}$, especially preferably $C_{1-12}$ heterocyclic oxy groups such as pyridyloxy, pyrazyloxy, pyrimidyloxy, and quinolyloxy), acyl groups (preferably $C_{1-30}$, more preferably $C_{1-20}$, especially preferably $C_{1-12}$ acyl groups such as acetyl, benzoyl, formyl, and pivaloyl), alkoxycarbonyl groups (preferably $C_{2-30}$, more preferably $C_{2-20}$, especially preferably $C_{2-12}$ alkoxycarbonyl groups such as methoxycarbonyl and ethoxycarbonyl), aryloxycarbonyl groups (preferably $C_{7-30}$, more preferably $C_{7-20}$, especially preferably $C_{7-12}$ aryloxycarbonyl groups such as phenyloxycarbonyl), acyloxy groups (preferably $C_{2-30}$, more preferably $C_{2-20}$, especially preferably $C_{2-10}$ acyloxy groups such as acetoxy and benzoyloxy), acylamino groups (preferably $C_{2-30}$, more preferably $C_{2-20}$, especially preferably $C_{2-10}$ acylamino groups such as acetylamino and benzoylamino), alkoxycarbonylamino groups (preferably $C_{2-30}$, more preferably $C_{2-20}$, especially preferably $C_{2-12}$ alkoxycarbonylamino groups such as methoxycarbonylamino), aryloxycarbonylamino groups (preferably $C_{7-30}$, more preferably $C_{7-20}$, especially preferably $C_{7-12}$ aryloxycarbonylamino groups such as phenyloxycarbonylamino), sulfonylamino groups (preferably $C_{1-30}$, more preferably $C_{1-20}$, especially preferably $C_{1-12}$ sulfonylamino groups such as methanesulfonylamino and benzenesulfonylamino), sulfamoyl groups (preferably $C_{0-30}$, more preferably $C_{0-20}$, especially preferably $C_{0-12}$ sulfamoyl groups such as sulfamoyl, methylsulfamoyl, dimethylsulfamoyl, and phenylsulfamoyl), carbamoyl groups (preferably $C_{1-30}$, more preferably $C_{1-20}$, especially preferably $C_{1-12}$ carbamoyl groups such as carbamoyl, methylcarbamoyl, diethylcarbamoyl, and phenylcarbamoyl), alkylthio groups (preferably $C_{1-30}$, more preferably $C_{1-20}$, especially preferably $C_{1-12}$ alkylthio groups such as methylthio and ethylthio), arylthio groups (preferably $C_{6-30}$, more preferably $C_{6-20}$, especially preferably $C_{6-12}$ arylthio groups such as phenylthio), heterocyclic thio groups (preferably $C_{1-30}$, more preferably $C_{1-20}$, especially preferably $C_{1-12}$ heterocyclic thio groups such as pyridylthio, 2-benzimidazolylthio, 2-benzoxazolylthio, and 2-benzthiazolylthio), sulfonyl groups (preferably $C_{1-30}$, more preferably $C_{1-20}$, especially preferably $C_{1-12}$ sulfonyl groups such as mesyl and tosyl), sulfinyl groups (preferably $C_{1-30}$, more preferably $C_{1-20}$, especially preferably $C_{1-12}$ sulfinyl groups such as methanesulfinyl and benzenesulfinyl), ureido groups (preferably $C_{1-30}$, more preferably $C_{1-20}$, especially preferably $C_{1-12}$ ureido groups such as ureido, methylureido, and phenylureido), phosphoric acid amide groups (preferably $C_{1-30}$, more preferably $C_{1-20}$, especially preferably $C_{1-12}$ phosphoric acid amide groups such as diethylphosphoric acid amide and phenylphosphoric acid amide), a hydroxy group, a mercapto group, halogen atoms (such as fluorine, chlorine, bromine, and iodine, more preferably fluorine), a cyano group, a sulfo group, a carboxyl group, a nitro group, a hydroxamic acid group, a sulfino group, a hydrazino group, an imino group, heterocyclic groups (preferably $C_{1-30}$, more preferably $C_{1-12}$ heterocyclic groups having, as a heteroatom, a nitrogen atom, an oxygen atom, a sulfur atom, or the like and specific examples include imidazolyl, pyridyl, quinolyl, furyl, thienyl, piperidyl, morpholino, benzoxazolyl, benzimidazolyl, benzothiazolyl, carbazolyl, and azepinyl), silyl groups (preferably $C_{3-40}$, more preferably $C_{3-30}$, especially preferably $C_{3-24}$ silyl groups such as trimethylsilyl and triphenylsilyl), and silyloxy groups $C_{3-40}$, more preferably $C_{3-30}$, especially preferably $C_{3-24}$ silyloxy groups such as trimethylsilyloxy and triphenylsilyloxy). These substituents each may have a further substituent, and the further substituent may be a substituent selected from Substituent group A specified above. Among them, when an alkyl group has a further substituent, the alkyl group is preferably a haloalkyl group substituted with a halogen atom(s) (preferably $C_{1-10}$ perfluoroalkyl groups, more preferably $C_{14}$ perfluoroalkyl groups, especially preferably a perfluoromethyl group).

The formula (I) is further illustrated. In the formula (I), N represents a nitrogen atom, C represents a carbon atom, and Pt represents a platinum atom. Each of $Z_1$, $Z_4$, $Z_5$ and $Z_8$ independently represents a substituted or unsubstituted carbon atom, or a nitrogen atom. Each of $Z_2$, $Z_3$, $Z_6$ and $Z_7$ independently represents a substituted or unsubstituted carbon atom, a substituted or unsubstituted nitrogen atom, an oxygen atom, or a sulfur atom. Of these atoms, a substituted or unsubstituted carbon atom, or a substituted or unsubstituted nitrogen atom is preferable to the others. The bond between each pair of adjacent atoms in the 5-membered rings, one of which is formed of $Z_1$, $Z_2$, $Z_3$, $Z_4$ and the nitrogen atom, and the other of which is formed of $Z_5$, $Z_6$, $Z_7$, $Z_8$ and the nitrogen atom, represents a single bond or a double bond, and the combination of bonds in each of the 5-membered rings may be any combination of single bonds and double bonds. Each of the 5-membered ring formed of $Z_1$, $Z_2$, $Z_3$, $Z_4$ and the nitrogen atom and the 5-membered ring formed of $Z_5$, $Z_6$, $Z_7$, $Z_8$ and the nitrogen atom is preferably a pyrazole ring, an imidazole ring, a triazole ring, an oxazole ring, a thiazole ring or a indazole ring, more preferably a pyrazole ring or an imidazole ring, still more preferably a pyrazole ring. In the formula (I), a single bond or a double bond is drawn by a double line composed of a solid line and a dotted line (and the same thing is said in the formula (II)). Additionally, the dotted line linking between Pt and each of the nitrogen atoms represents a coordinate bond.

In the formula (I), when $Z_1$, $Z_2$, $Z_3$, $Z_4$, $Z_5$, $Z_6$, $Z_7$, and $Z_8$ can have a substituent, they may independently have a substituent selected from Substituent group A. Preferred examples of the substituent include the alkyl groups, the cycloalkyl groups, the aryl groups, the amino groups, the alkoxy groups, the aryloxy groups, the acyl groups, the alkoxycarbonyl groups, the aryloxycarbonyl groups, the aryloxy groups, the sulfonylamino groups, the sulfamoyl groups, the carbamoyl groups, the alkylthio groups, the arylthio groups, the heterocyclic thio groups, the sulfonyl groups, the sulfinyl groups, the ureido groups, the phosphoric acid amide groups, the hydroxy group, the mercapto group, the halogen atoms, the sulfo group, the carboxyl group, the nitro group, the sulfino group, the heterocyclic groups, and the silyl groups. Of these, the substituted or unsubstituted alkyl groups, the cycloalkyl groups, the aryl groups, the amino groups, the alkoxy groups, the aryloxy groups, the cyano group, and the heterocyclic groups are more preferred, the alkyl groups, the aryl groups and the cyano group are still more preferred, and the trifluoromethyl group, the phenyl group and the cyano group are most preferred.

In the formula (I), each of $Z_{11}$ and $Z_{16}$ independently represents a substituted or unsubstituted carbon atom or a substituted or unsubstituted nitrogen atom, while each of $Z_{12}$, $Z_{13}$, $Z_{14}$, $Z_{15}$, $Z_{17}$, $Z_{18}$, $Z_{19}$, and $Z_{20}$ independently represents a substituted or unsubstituted carbon atom, a nitrogen atom, an oxygen atom, and a sulfur atom, preferably a substituted or unsubstituted carbon atom or a nitrogen atom, more preferably a substituted or unsubstituted carbon atom. Each bond between atoms of a 6-membered ring formed by $Z_{11}$, $Z_{12}$, $Z_{13}$, $Z_{14}$, $Z_{15}$ and a carbon atom and each bond between atoms of a 6-membered ring formed by $Z_{16}$, $Z_{17}$, $Z_{18}$, $Z_{19}$, $Z_{20}$, and a carbon atom represents a single bond or a double bond. These bonds between two atoms may be any combination of a single bond and a double bond. $Z_{12}$ and $Z_{13}$, $Z_{13}$ and $Z_{14}$, $Z_{17}$ and $Z_{18}$, or $Z_{18}$ and $Z_{19}$ may be coupled together via a substituent to form a ring fused structure, at least one pair selected from $Z_{12}$ and $Z_{13}$, $Z_{13}$ and $Z_{14}$, $Z_{17}$ and $Z_{18}$, and $Z_{18}$ and $Z_{19}$ may form a 5-membered ring via a substituent. When $Z_{12}$ and $Z_{13}$, $Z_{13}$ and $Z_{14}$, $Z_{17}$ and $Z_{18}$, or $Z_{18}$ and $Z_{19}$ form a 5-membered ring via a substituent, the 5-membered ring may have another ring fused structure. This means that at least one of the 6-membered ring formed by $Z_{11}$, $Z_{12}$, $Z_{13}$, $Z_{14}$, $Z_{15}$, and a carbon atom and the 6-membered ring formed by $Z_{16}$, $Z_{17}$, $Z_{18}$, $Z_{19}$, $Z_{20}$, and a carbon atom forms a fused ring (with a 5-membered ring or a 5-membered ring fused with a 6-membered ring). The fused ring formed by $Z_{11}$, $Z_{12}$, $Z_{13}$, $Z_{14}$, $Z_{15}$ and a carbon atom or the fused ring formed by $Z_{16}$, $Z_{17}$, $Z_{18}$, $Z_{19}$, $Z_{20}$, and a carbon atom is bicyclic (fused with a 5-membered ring) or tricyclic (fused with a 5-membered ring fused with a 6-membered ring), more preferably a benzofuran ring, a dibenzofuran ring, an indole ring, an indazole ring, a benzimidazole ring, a carbazole ring, a benzothiophene ring, a dibenzothiophene ring, a benzothiazole ring, or a benzoxazole ring, still more preferably a dibenzofuran ring, a carbazole ring, or a dibenzothiophene ring, most preferably a dibenzofuran ring. When these fused rings are replaceable, they may have a substituent selected from Substituent group A. Preferred examples of the substituent include the alkyl groups, the cycloalkyl groups, the aryl groups, the amino groups, the alkoxy groups, the aryloxy groups, the acyl groups, the alkoxycarbonyl groups, the aryloxycarbonyl groups, the acyloxy groups, the sulfonylamino groups, the sulfamoyl groups, the carbamoyl groups, the alkylthio groups, the arylthio groups, the heterocyclic thio groups, the sulfonyl groups, the sulfinyl groups, the ureido groups, the phosphoric acid amide groups, the hydroxy group, the mercapto group, the halogen atoms, the cyano group, the sulfo group, the carboxyl group, the nitro group, the sulfino group, the heterocyclic groups, and the silyl groups. Of these, the substituted or unsubstituted alkyl groups, the cycloalkyl groups, the aryl groups, the amino groups, the alkoxy groups, the aryloxy groups, the cyano group, and the heterocyclic groups are more preferred, the alkyl groups, the aryl groups, and the cyano group are still more preferred, and the tert-butyl group, the trifluoromethyl group, the phenyl group and the cyano group are most preferred.

In the formula (I), each of $Y_1$ and $Y_2$ independently represents a single bond, an oxygen atom, a sulfur atom, a nitrogen atom which may have a substituent selected from Substituent group A, or an unsubstituted nitrogen atom, preferably a single bond, an oxygen atom, or a sulfur atom, preferably a single bond, an oxygen atom, or a sulfur atom, more preferably a single bond. When each of $Y_1$ and $Y_2$ independently represents a substituted nitrogen atom, the substituent is preferably selected from Substituent group A, more preferably an alkyl group, a cycloalkyl group, or an aryl group, still more preferably a $C_{1-7}$ alkyl group or a $C_{6-12}$ (the number of rings: 1 or 2) aryl group.

In the formula (I), $A_{11}$ represents a divalent linking group. Although the linking group is not particularly limited, a divalent linking group composed of a single bond, a carbon atom, a nitrogen atom, an oxygen atom, a sulfur atom, a silicon atom, or a germanium atom is especially preferred, with the group selected from the following Group A of linking groups is especially preferred. Group A of linking groups

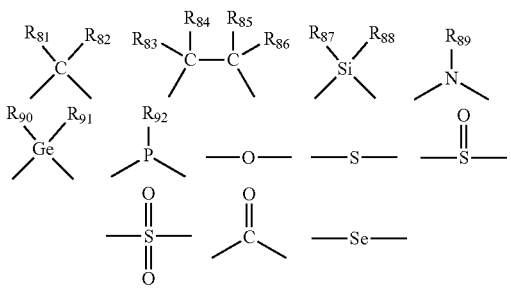

In Group A of linking groups, each of $R_{81}$, $R_{82}$, $R_{83}$, $R_{84}$, $R_{85}$, $R_{86}$, $R_{87}$, $R_{88}$, $R_{89}$, $R_{90}$, $R_{91}$, and $R_{92}$ ($R_{81}$ to $R_{92}$) independently represents a hydrogen atom or a substituent. When each of $R_{81}$ to $R_{92}$ independently represents a substituent, the substituent is preferably selected from Substituent group A. When each of $R_{81}$ to $R_{92}$ is replaceable, it may have a substituent further, or $R_{81}$ and $R_{82}$, $R_{83}$ and $R_{84}$, $R_{85}$ and $R_{86}$, $R_{83}$ and $R_{85}$, $R_{83}$ and $R_{86}$, $R_{84}$ and $R_{86}$, or $R_{90}$ and $R_{91}$ may be coupled together to form a ring.

$A_{11}$ is preferably a substituent selected from Group A of linking groups. Of these, —C($R_{81}$)($R_{82}$)—, —C($R_{83}$)($R_{84}$)C($R_{85}$)($R_{86}$)—, —Si($R_{87}$)($R_{88}$)—, —N($R_{89}$)—, —O—, —S—, —SO—, —SO$_2$—, and —CO— are preferred, of which —C($R_{81}$)($R_{82}$)—, —C($R_{83}$)($R_{84}$)C($R_{85}$)($R_{86}$)—, —Si($R_{87}$)($R_{88}$)—, —O—, and —S— are more preferred and —C($R_{81}$)($R_{82}$)— and —C($R_{83}$)($R_{84}$)C($R_{85}$)($R_{86}$)— are still more preferred.

In the —C($R_{81}$)($R_{82}$)—, each of $R_{81}$ and $R_{82}$ preferably represents a hydrogen atom or a substituent selected from the following Substituent group B.

(Substituent Group B)

Substituent group B includes alkyl groups, cycloalkyl groups, aryl groups, halogen atoms, amino groups, alkylthio groups, arylthio groups, alkyloxy groups, aryloxy groups, a hydroxy group, a mercapto group, and halogen atoms, of which alkyl groups, cycloalkyl groups, aryl groups, halogen atoms, alkylthio groups, arylthio groups, alkyloxy groups, aryloxy groups and halogen atoms are more preferred, with alkyl groups and aryl groups being still more preferred.

In the —C($R_{83}$)($R_{84}$)C($R_{85}$)($R_{86}$)—, each of $R_{83}$, $R_{84}$, $R_{85}$, and $R_{86}$ preferably represents a hydrogen atom or a substituent selected from Substituent group B.

In the —Si($R_{87}$)($R_{88}$)—, each of $R_{87}$ and $R_{88}$ preferably represents a hydrogen atom or a substituent selected from Substituent group B.

In the —Ge($R_{90}$)($R_{91}$)—, each of $R_{90}$ and $R_{91}$ preferably represents a hydrogen atom or a substituent selected from Substituent group B.

In the —N($R_{89}$)—, $R_{89}$ preferably represents a hydrogen atom, an alkyl group, a cycloalkyl group, or an aryl group, more preferably an alkyl group or an aryl group, still more preferably an aryl group.

In the —P($R_{92}$)—, a preferable range of $R_{92}$ is similar to that of $R_{89}$.

In the formula (I), each of $B_1$ and $B_2$ represents a single bond or a divalent linking group. The linking group is not particularly limited, but is preferably a single bond or a divalent linking group composed of a carbon atom, a nitrogen atom, an oxygen atom, a sulfur atom, a silicon atom, or a germanium atom, more preferably a single bond or a group selected from Group A of linking groups, more preferably a single bond, —C($R_{81}$)($R_{82}$)—, —C($R_{83}$)($R_{84}$)C($R_{85}$)($R_{86}$)—, —Si($R_{87}$)($R_{88}$)—, —N($R_{89}$)—, —O—, —S—, or —CO—, especially preferably a single bond, —C($R_{81}$)($R_{82}$)—, or —O—. When $B_1$ represents —C($R_{81}$)($R_{82}$)—, —C($R_{83}$)($R_{84}$)C($R_{85}$)($R_{86}$)—, —Si($R_{87}$)($R_{88}$)—, —Ge($R_{90}$)($R_{91}$)—, —N($R_{89}$)—, or P($R_{92}$)—, a preferable range of it is similar to that in the above description of $A_{11}$.

Relationships between the formulae in the invention are as follows: The formula (I) is preferably the formula (II) or the formula (III), the formula (II) is preferably the formula (IV), the formula (III) is preferably the formula (V), the formula (IV) is preferably the following formula (VI), and the formula (V) is preferably the following formula (VII).

The formula (II) is illustrated below:

Formula (II)

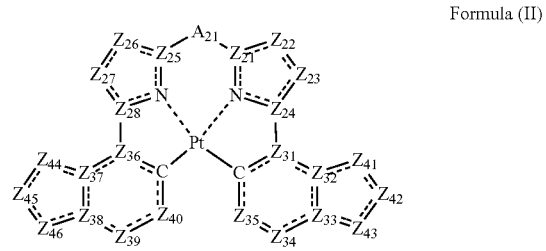

(wherein N represents a nitrogen atom, C represents a carbon atom, and Pt represents a platinum atom; each of $Z_{21}$, $Z_{24}$, $Z_{25}$ and $Z_{28}$ independently represents a substituted or unsubstituted carbon atom, or a nitrogen atom; each of $Z_{22}$, $Z_{23}$, $Z_{26}$ and $Z_{27}$ independently represents a substituted or unsubstituted carbon atom, a substituted or unsubstituted nitrogen atom, an oxygen atom, or a sulfur atom; the bond between each pair of adjacent atoms in the 5-membered rings, one of which is formed of $Z_{21}$, $Z_{22}$, $Z_{23}$, $Z_{24}$ and the nitrogen atom, and the other of which is formed of $Z_{25}$, $Z_{26}$, $Z_{27}$, $Z_{28}$ and the nitrogen atom, represents a single bond or a double bond; when $Z_{21}$, $Z_{22}$, $Z_{23}$, $Z_{24}$, $Z_{25}$, $Z_{26}$, $Z_{27}$ and $Z_{28}$ can have substituents, each of them may have a substituent selected individually from Substituent group A; each of $Z_{34}$, $Z_{35}$, $Z_{39}$ and $Z_{40}$ independently represents a substituted or unsubstituted carbon atom, a substituted or unsubstituted nitrogen atom, an oxygen atom, or a sulfur atom; each of $Z_{41}$, $Z_{42}$, $Z_{43}$, $Z_{44}$, $Z_{45}$ and $Z_{46}$ independently represents a substituted or unsubstituted carbon atom, a substituted or unsubstituted nitrogen atom, an oxygen atom, a sulfur atom, a selenium atom or a tellurium atom; each of $Z_{31}$, $Z_{32}$, $Z_{33}$, $Z_{36}$, $Z_{37}$ and $Z_{38}$ independently represents a substituted or unsubstituted carbon atom, or a nitrogen atom; the bond between each pair of adjacent atoms in the (6-membered+5-membered) fused rings, one of which is formed of $Z_{31}$, $Z_{32}$, $Z_{33}$, $Z_{34}$, $Z_{35}$, $Z_{41}$, $Z_{42}$, $Z_{43}$ and the carbon atom, and the other of which is formed of $Z_{36}$, $Z_{37}$, $Z_{38}$, $Z_{39}$, $Z_{40}$, $Z_{44}$, $Z_{45}$, $Z_{46}$ and the carbon atom, represents a single bond or a double bond; each pair of adjacent members of the 5-membered rings, $Z_{41}$ and $Z_{42}$, $Z_{42}$ and $Z_{43}$, $Z_{44}$ and $Z_{45}$, or $Z_{45}$ and $Z_{46}$, may combine together to form a ring; when $Z_{31}$, $Z_{32}$, $Z_{33}$, $Z_{34}$, $Z_{35}$, $Z_{36}$, $Z_{37}$, $Z_{38}$, $Z_{39}$, $Z_{40}$, $Z_{41}$, $Z_{42}$, $Z_{43}$, $Z_{44}$, $Z_{45}$ and $Z_{46}$ can have substituents, each of them may have a substituent selected individually from Substituent group A; and $A_{21}$ represents a divalent linking group).

$Z_{21}$, $Z_{22}$, $Z_{23}$, $Z_{24}$, $Z_{25}$, $Z_{26}$, $Z_{27}$ and $Z_{28}$ in the formula (II) have the same meanings as $Z_1$, $Z_2$, $Z_3$, $Z_4$, $Z_5$, $Z_6$, $Z_7$ and $Z_8$ in the formula (I), respectively, and the preferred ranges thereof are similar to those of $Z_1$, $Z_2$, $Z_3$, $Z_4$, $Z_5$, $Z_6$, $Z_7$ and $Z_8$ in the formula (I), respectively.

In the formula (II), each of $Z_{34}$, $Z_{35}$, $Z_{39}$ and $Z_{40}$ independently represents a substituted or unsubstituted carbon atom, a substituted or unsubstituted nitrogen atom, an oxygen atom or a sulfur atom, preferably a substituted or unsubstituted carbon atom or a substituted or unsubstituted nitrogen atom, more preferably a substituted or unsubstituted carbon atom, still more preferably an unsubstituted carbon atom. Each of $Z_{31}$, $Z_{32}$, $Z_{33}$, $Z_{36}$, $Z_{37}$ and $Z_{38}$ independently represents a substituted or unsubstituted carbon atom, or a nitrogen atom, preferably a substituted or unsubstituted carbon atom, more preferably an unsubstituted carbon atom. Each of $Z_{41}$, $Z_{42}$, $Z_{43}$, $Z_{44}$, $Z_{45}$ and $Z_{46}$ independently represents a substituted or unsubstituted carbon atom, a substituted or unsubstituted nitrogen atom, an oxygen atom, a sulfur atom, a selenium atom or a tellurium atom, preferably a substituted or unsubstituted carbon atom, a substituted or unsubstituted nitrogen atom, an oxygen atom or a sulfur atom, more preferably a substituted or unsubstituted carbon atom, an oxygen atom or a sulfur atom, still more preferably a substituted or unsubstituted carbon atom, or an oxygen atom. The bond between each pair of adjacent atoms in the (6-membered+5-membered) fused rings, one of which is formed of $Z_{31}$, $Z_{32}$, $Z_{33}$, $Z_{34}$, $Z_{35}$, $Z_{41}$, $Z_{42}$, $Z_{43}$ and the carbon atom, and the other of which is formed of $Z_{36}$, $Z_{37}$, $Z_{38}$, $Z_{39}$, $Z_{40}$, $Z_{44}$, $Z_{45}$, $Z_{46}$ and the carbon atom, represents a single bond or a double bond, and the combination of bonds in each of those fused rings may be any combination of single bonds and double bonds. Each of the (6-membered+5-membered) fused ring formed of $Z_{31}$, $Z_{32}$, $Z_{33}$, $Z_{34}$, $Z_{35}$, $Z_{41}$, $Z_{42}$, $Z_{43}$ and the carbon atom and the (6-membered+5-membered) fused ring formed of $Z_{36}$, $Z_{37}$, $Z_{38}$, $Z_{39}$, $Z_{40}$, $Z_{44}$, $Z_{45}$, $Z_{46}$ and the carbon atom is preferably a benzofuran ring, a dibenzofuran ring, an indole ring, an indazole ring, a benzimidazole ring, a carbazole ring, a benzothiophene ring, a dibenzothiophene ring, a benzothiazole ring or a benzoxazole ring, more preferably a dibenzofuran ring, a benzimidazole ring, a carbazole ring, a dibenzothiophene ring, a benzothiazole ring or a benzoxazole ring, still more preferably a dibenzofuran ring or a dibenzothiophene ring, most preferably a dibenzofuran ring. When these rings can have substituents, each substituent can be selected individually from Substituent group A. The substituents preferred by these rings are similar to the substituents which the fused ring formed of $Z_{11}$, $Z_{12}$, $Z_{13}$, $Z_{14}$, $Z_{15}$ and the carbon atom or the fused ring formed of $Z_{16}$, $Z_{17}$, $Z_{18}$, $Z_{19}$, $Z_{20}$ and the carbon atom has in the formula (I).

$A_{21}$ in the formula (II) has the same meaning as $A_{11}$ has in the formula (I), and the preferred range thereof is similar to that of $A_{11}$ in the formula (I).

The formula (III) is illustrated below:

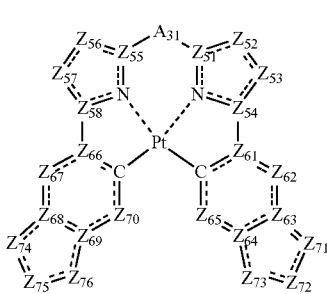

Formula (III)

(wherein N represents a nitrogen atom, C represents a carbon atom, and Pt represents a platinum atom; each of $Z_{51}$, $Z_{54}$, $Z_{55}$ and $Z_{58}$ independently represents a substituted or unsubstituted carbon atom, or a nitrogen atom; each of $Z_{52}$, $Z_{53}$, $Z_{56}$ and $Z_{57}$ independently represents a substituted or unsubstituted carbon atom, a substituted or pair of adjacent atoms in the 5-membered rings, one of which is formed of $Z_{51}$, $Z_{52}$, $Z_{53}$, $Z_{54}$ and the nitrogen atom, and the other of which is formed of $Z_{55}$, $Z_{56}$, $Z_{57}$, $Z_{58}$ and the nitrogen atom, represents a single bond or a double bond; when $Z_{51}$, $Z_{52}$, $Z_{53}$, $Z_{54}$, $Z_{55}$, $Z_{56}$, $Z_{57}$ and $Z_{58}$ can have substituents, each of them may have a substituent selected individually from Substituent group A; each of $Z_{62}$, $Z_{65}$, $Z_{67}$ and $Z_{70}$ independently represents a substituted or unsubstituted carbon atom, a substituted or unsubstituted nitrogen atom, an oxygen atom, or a sulfur atom; each of $Z_{71}$, $Z_{72}$, $Z_{73}$, $Z_{74}$, $Z_{75}$ and $Z_{76}$ independently represents a substituted or unsubstituted carbon atom, a substituted or unsubstituted nitrogen atom, an oxygen atom, a sulfur atom, a selenium atom or a tellurium atom; each of $Z_{61}$, $Z_{63}$, $Z_{64}$, $Z_{66}$, $Z_{68}$ and $Z_{69}$ independently represents a substituted or unsubstituted carbon atom, or a nitrogen atom; the bond between each pair of adjacent atoms in the (6-membered+5-membered) fused rings, one of which is formed of $Z_{61}$, $Z_{62}$, $Z_{63}$, $Z_{64}$, $Z_{65}$, $Z_{71}$, $Z_{72}$, $Z_{73}$ and the carbon atom, and the other of which is formed of $Z_{66}$, $Z_{67}$, $Z_{68}$, $Z_{69}$, $Z_{70}$, $Z_{74}$, $Z_{75}$, $Z_{76}$ and the carbon atom, represents a single bond or a double bond; each pair of adjacent members of the 5-membered rings, $Z_{71}$ and $Z_{72}$, $Z_{72}$ and $Z_{73}$, $Z_{74}$ and $Z_{75}$, or $Z_{75}$ and $Z_{76}$, may combine together to form a ring; when $Z_{61}$, $Z_{62}$, $Z_{63}$, $Z_{64}$, $Z_{65}$, $Z_{66}$, $Z_{67}$, $Z_{68}$, $Z_{69}$, $Z_{70}$, $Z_{71}$, $Z_{72}$, $Z_{73}$, $Z_{74}$, $Z_{75}$ and $Z_{76}$ can have substituents, each of them may have a substituent selected individually from Substituent group A; and $A_{31}$ represents a divalent linking group).

$Z_{51}$, $Z_{52}$, $Z_{53}$, $Z_{54}$, $Z_{55}$, $Z_{56}$, $Z_{57}$ and $Z_{58}$ in the formula (III) have the same meanings as $Z_1$, $Z_2$, $Z_3$, $Z_4$, $Z_5$, $Z_6$, $Z_7$ and $Z_8$ in the formula (I), respectively, and the preferred ranges thereof are similar to those of $Z_1$, $Z_2$, $Z_3$, $Z_4$, $Z_5$, $Z_6$, $Z_7$ and $Z_8$ in the formula (I), respectively.

In the formula (III), each of $Z_{62}$, $Z_{65}$, $Z_{67}$ and $Z_{70}$ independently represents a substituted or unsubstituted carbon atom, a substituted or unsubstituted nitrogen atom, an oxygen atom or a sulfur atom, preferably a substituted or unsubstituted carbon atom or a substituted or unsubstituted nitrogen atom, more preferably a substituted or unsubstituted carbon atom, still more preferably an unsubstituted carbon atom. Each of $Z_{61}$, $Z_{63}$, $Z_{64}$, $Z_{66}$, $Z_{68}$ and $Z_{69}$ independently represents a substituted or unsubstituted carbon atom, or a nitrogen atom, preferably a substituted or unsubstituted carbon atom, more preferably an unsubstituted carbon atom. Each of $Z_{71}$, $Z_{72}$, $Z_{73}$, $Z_{74}$, $Z_{75}$ and $Z_{76}$ independently represents a substituted or unsubstituted carbon atom, a substituted or unsubstituted nitrogen atom, an oxygen atom, a sulfur atom, a selenium atom or a tellurium atom, preferably a substituted or unsubstituted carbon atom, a nitrogen atom, an oxygen atom or a sulfur atom, more preferably a substituted or unsubstituted carbon atom, an oxygen atom or a sulfur atom, still more preferably a substituted or unsubstituted carbon atom or an oxygen atom. The bond between each pair of adjacent atoms in the (6-membered+5-membered) fused rings, one of which is formed of $Z_{61}$, $Z_{62}$, $Z_{63}$, $Z_{64}$, $Z_{65}$, $Z_{71}$, $Z_{72}$, $Z_{73}$ and the carbon atom, and the other of which is formed of $Z_{66}$, $Z_{67}$, $Z_{68}$, $Z_{69}$, $Z_{70}$, $Z_{74}$, $Z_{75}$, $Z_{76}$ and the carbon atom, represents a single bond or a double bond, and the combination of bonds in each of those fused rings may be any combination of single bonds and double bonds. Each of the (6-membered+5-membered) fused ring formed of $Z_{61}$, $Z_{62}$, $Z_{63}$, $Z_{64}$, $Z_{65}$, $Z_{71}$, $Z_{72}$, $Z_{73}$ and the carbon atom and the (6-membered+5-membered) fused ring formed of $Z_{66}$, $Z_{67}$, $Z_{68}$, $Z_{69}$, $Z_{70}$, $Z_{74}$, $Z_{75}$, $Z_{76}$ and the carbon atom is preferably a benzofuran ring, a dibenzofuran ring, an indole ring, an indazole ring, a benzimidazole ring, a carbazole ring, a benzothiophene ring, a dibenzothiophene ring, a benzothiazole ring or a benzoxazole ring, more preferably a dibenzofuran ring, a benzimidazole ring, a carbazole ring, a dibenzothiophene ring, a benzothiazole ring or a benzoxazole ring, still more preferably a dibenzofuran ring or a dibenzothiophene ring, most preferably a dibenzofuran ring. When these rings can further have substituents, each substituent can be selected independently from Substituent group A. The substituents preferred by these rings are similar to the substituents which the fused ring formed of $Z_{11}$, $Z_{125}$ $Z_{13}$, $Z_{14}$, $Z_{15}$ and the carbon atom or the fused ring formed of $Z_{16}$, $Z_{17}$, $Z_{18}$, $Z_{19}$, $Z_{20}$ and the carbon atom has in the formula (I).

$A_{31}$ in the formula (III) has the same meaning as $A_{11}$ has in the formula (I), and the preferred range thereof is similar to that of $A_{11}$ in the formula (I).

The formula (IV) is illustrated below:

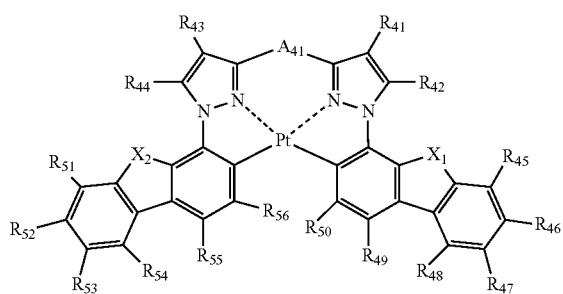

Formula (IV)

(wherein each of $X_1$ and $X_2$ independently represents a substituted or unsubstituted carbon atom, a substituted or unsubstituted nitrogen atom, an oxygen atom, a sulfur atom or a selenium atom; each of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ independently represents a hydrogen atom or a substituent selected from Substituent group A; and $A_{41}$ represents a divalent linking group).

In the formula (IV), each of $X_1$ and $X_2$ independently represents a substituted or unsubstituted carbon atom, a substituted or unsubstituted nitrogen atom, an oxygen atom, a sulfur atom or a selenium atom, preferably a substituted or unsubstituted carbon atom, a substituted or unsubstituted nitrogen atom, an oxygen atom or a sulfur atom, more preferably a substituted or unsubstituted nitrogen atom, an oxygen atom or a sulfur atom, still more preferably an oxygen atom or a sulfur atom, most preferably an oxygen atom.

In the formula (IV), each of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ independently represents a hydrogen atom or a substituent selected from Substituent group A, and when it further has a substituent, the substituent is preferably selected from Substituent group A. Each of $R_{41}$, $R_{42}$, $R_{43}$, $R_{44}$ is preferably a hydrogen atom, a substituted or unsubstituted alkyl group, a cycloalkyl group, an aryl group, an amino group, an alkoxy group, an aryloxy group, a heterocyclic group, a cyano group or a silyl group, more preferably a hydrogen atom, a substituted or unsubstituted alkyl group, a cycloalkyl group, an aryl group, an amino group or a cyano group, still more preferably a hydrogen atom, an alkyl group, an aryl group or a cyano group, most preferably a hydrogen atom, a trifluoromethyl group, a phenyl group or a cyano group. Each of $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ is preferably a hydrogen atom, a substituted or unsubstituted alkyl group, a cycloalkyl group, an aryl group, an amino group, an alkoxy group, an aryloxy group, a heterocyclic group, a cyano group or a silyl group, more preferably a hydrogen atom, a substituted or unsubstituted alkyl group, an aryl group or a cyano group, still more preferably a hydrogen atom, a trifluoromethyl group, a phenyl group or a cyano group, most preferably a hydrogen atom.

$A_{41}$ in the formula (IV) has the same meaning as $A_{11}$ has in the formula (I), and the preferred range thereof is similar to that of $A_{11}$ in the formula (I).

The formula (V) is illustrated below:

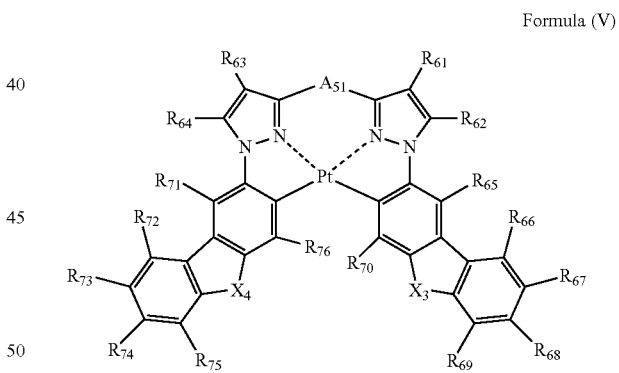

Formula (V)

(wherein each of $X_3$ and $X_4$ independently represents a substituted or unsubstituted carbon atom, a substituted or unsubstituted nitrogen atom, an oxygen atom, a sulfur atom or a selenium atom; each of $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$ and $R_{76}$ independently represents a hydrogen atom or a substituent selected from Substituent group A; and $A_{51}$ represents a divalent linking group).

In the formula (V), each of $X_3$ and $X_4$ independently represents a substituted or unsubstituted carbon atom, a substituted or unsubstituted nitrogen atom, an oxygen atom, a sulfur atom or a selenium atom, preferably a substituted or unsubstituted carbon atom, a substituted or unsubstituted nitrogen atom, an oxygen atom or a sulfur atom, more preferably a substituted or unsubstituted nitrogen atom, an oxygen atom or a sulfur atom, still more preferably an oxygen atom or a sulfur atom, most preferably an oxygen atom.

In the formula (V), each of $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$ and $R_{76}$ independently represents a hydrogen atom or a substituent selected from Substituent group A, and when it further has a substituent, the substituent is preferably selected from Substituent group A. The preferred ranges of $R_{61}$, $R_{62}$, $R_{63}$ and $R_{64}$ are similar to those of $R_{41}$, $R_{42}$, $R_{43}$ and $R_{44}$ in the formula (IV). Each of $R_{65}$, $R_{66}$, $R_{68}$, $R_{69}$, $R_{70}$, $R_{71}$, $R_{72}$, $R_{74}$, $R_{75}$ and $R_{76}$ is preferably a hydrogen atom, a substituted or unsubstituted alkyl group, a cycloalkyl group, an aryl group, an amino group, an alkoxy group, an aryloxy group, a heterocyclic group, a cyano group or a silyl group, more preferably a hydrogen atom, a substituted or unsubstituted alkyl group, an aryl group or a cyano group, still more preferably a hydrogen atom, a trifluoromethyl group, a phenyl group or a cyano group, most preferably a hydrogen atom. Each of $R_{67}$ and $R_{73}$ is preferably a hydrogen atom, a substituted or unsubstituted alkyl group, a cycloalkyl group, an aryl group, an amino group, an alkoxy group, an aryloxy group, a heterocyclic group, a cyano group or a silyl group, more preferably a hydrogen atom, a substituted or unsubstituted alkyl group, a cycloalkyl group, an aryl group, an amino group or a cyano group, still more preferably a hydrogen atom, an alkyl group, an aryl group or a cyano group, most preferably a hydrogen atom, a tert-butyl group, a trifluoromethyl group, a phenyl group or a cyano group.

$A_{51}$ in the formula (V) has the same meaning as $A_{11}$ has in the formula (I), and the preferred range thereof is similar to that of $A_{11}$ in the formula (I).

The formula (VI) is illustrated below:

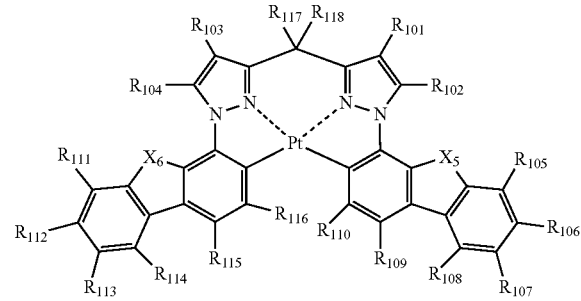

Formula (VI)

(wherein each of $X_5$ and $X_6$ independently represents an oxygen atom or a sulfur atom, each of $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $R_{115}$ and $R_{116}$ independently represents a hydrogen atom or a substituent selected from Substituent group A, and $R_{117}$ and $R_{118}$ represent alkyl groups, cycloalkyl groups or aryl groups).

In the formula (VI), though each of $X_5$ and $X_6$ independently may represent an oxygen atom or a sulfur atom, it is preferable that both $X_5$ and $X_6$ are oxygen atoms or sulfur atoms, and it is more preferable that both $X_5$ and $X_6$ are oxygen atoms.

In the formula (VI), each of $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $R_{115}$ and $R_{116}$ independently represents a hydrogen atom or a substituent selected from Substituent group A, and when it further has a substituent, the substituent is preferably selected from Substituent group A. The preferred ranges thereof are similar to those of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ in the formula (IV). Each of $R_{117}$ and $R_{118}$ independently represents a hydrogen atom, an alkyl group, a cycloalkyl group, an aryl group, a halogen atom, an amino group, an alkylthio group, an arylthio group, an alkyloxy group, an aryloxy group, a hydroxyl group, a mercapto group or a halogen atom, preferably a hydrogen atom, an alkyl group, a cycloalkyl group, an aryl group, a halogen atom, an alkylthio group, an arylthio group, an alkyloxy group or an aryloxy group, still more preferably an alkyl group, a cycloalkyl group or an aryl group, most preferably a methyl group.

The formula (VII) is illustrated below:

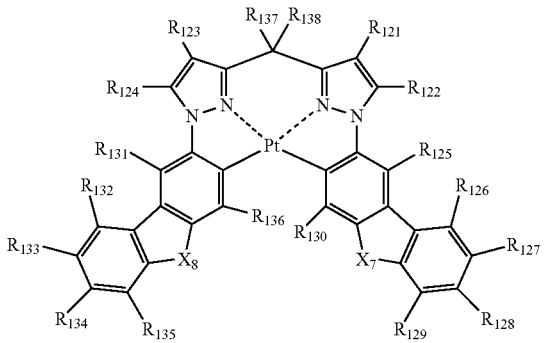

Formula (VII)

(wherein each of $X_7$ and $X_8$ independently represents an oxygen atom or a sulfur atom, each of $R_{121}$, $R_{122}$, $R_{123}$, $R_{124}$, $R_{125}$, $R_{126}$, $R_{127}$, $R_{128}$, $R_{129}$, $R_{130}$, $R_{131}$, $R_{132}$, $R_{133}$, $R_{134}$, $R_{135}$ and $R_{136}$ independently represents a hydrogen atom or a substituent selected from Substituent group A, and $R_{137}$ and $R_{138}$ represent alkyl groups, cycloalkyl groups or aryl groups).

In the formula (VII), though each of $X_7$ and $X_8$ independently may represent an oxygen atom or a sulfur atom, it is preferable that both $X_7$ and $X_8$ are oxygen atoms or sulfur atoms, and it is more preferable that both $X_7$ and $X_8$ are oxygen atoms.

In the formula (VII), each of $R_{121}$, $R_{122}$, $R_{123}$, $R_{124}$, $R_{125}$, $R_{126}$, $R_{127}$, $R_{128}$, $R_{129}$, $R_{130}$, $R_{131}$, $R_{132}$, $R_{133}$, $R_{134}$, $R_{135}$ and $R_{136}$ independently represents a hydrogen atom or a substituent selected from Substituent group A, and when it further has a substituent, the substituent is preferably selected from Substituent group A. The preferred ranges thereof are similar to those of $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$ and $R_{76}$ in the formula (V). Each of $R_{137}$ and $R_{138}$ independently represents a hydrogen atom, an alkyl group, a cycloalkyl group, an aryl group, a halogen atom, an amino group, an alkylthio group, an arylthio group, an alkyloxy group, an aryloxy group, a hydroxy group or a mercapto group, preferably a hydrogen atom, an alkyl group, a cycloalkyl group, an aryl group, a halogen atom, an alkylthio group, an arylthio group, an alkyloxy group or an aryloxy group, still more preferably an alkyl group, a cycloalkyl group or an aryl group, most preferably a methyl group.

The compound of the invention may be a low molecular compound, an oligomer compound, or a polymer compound (having a weight average molecular weight (in terms of polystyrene) of preferably from 1000 to 5000000, more preferably from 2000 to 1000000, still more preferably from 3000 to 100000). When it is the oligomer compound or the polymer compound, it may contain, in the main chain or a side chain thereof, the structure represented by the formula. The polymer compound may be either a homopolymer compound or a copolymer. The compound of the invention is preferably a low molecular compound.

The compound of the invention can be used for organic layers of an organic electroluminescence device. It can be used as any of a hole injection material, a hole transporting material, an electron transporting material, a hole blocking material, an electron blocking material, an exciton blocking material, and a light emitting material. The compound of the invention is used preferably as a hole injection material, a hole transporting material, an electron blocking material, or a light emitting material, more preferably as a hole transporting material and a light emitting material, still more preferably as a light emitting material.

When the compound of the invention is used as a light emitting material, it may be a ultraviolet light emitting material, a visible light emitting material, or an infrared ray emitting material. Or, it may be a fluorescent material or a phosphorescent material.

When the compound of the invention is used for a light emitting layer, it is usually contained in an amount of from 0.1 to 50 mass % based on the mass of all the compounds constituting the light emitting layer. From the viewpoints of durability and external quantum efficiency, it is contained preferably in an amount of from 1 to 50 mass %, more preferably from 2 to 40 mass %.

The host material contained in the device of the invention has lowest excited triplet ($T_1$ level) energies, in the form of a single film, of preferably 61 kcal/mol or greater (255.5 KJ/mol or greater) and 90 kcal/mol or less (377.1 KJ/mol or less), more preferably 62 kcal/mol or greater (259.78 KJ/mol or greater) and 85 kcal/mol or less (356.15 KJ/mol or less), still more preferably 65 kcal/mol or greater (272.35 KJ/mol or greater) and not greater than 80 kcal/mol or less (335.2 KJ/mol or less).

The $T_1$ level in the form of a single film can be determined from the short-wavelength end of a phosphorescence spectrum of a thin film of the material which has been obtained by measurement. The $T_1$ level in solution form can be determined from the short wavelength end of a phosphorescent spectrum of the material in the form of a solution which has been obtained by measurement. The term "$T_1$" as used herein means $T_1$ in the form of a thin film unless otherwise particularly specified.

The $T_1$ energies can be determined by depositing a material on a cleaned quartz glass substrate by vacuum deposition to form a film of about 50 nm, measuring the phosphorescence spectrum of the thin film at a liquid nitrogen temperature by using "F-7000 Fluorescence Spectrophotometer" (trade name; product of Hitachi High-Technologies), and converting the rising wavelength on the short wavelength side of the resulting phosphorescence spectrum to its equivalent in energy unit.

<Synthesis Process of the Compound of the Invention>

The compound of the invention can be synthesized by various processes. For example, it can be obtained by placing, at room temperature, or heating (heating with a mantle heater or microwave is effective as well as ordinary heating) a ligand or a dissociated product thereof and a platinum-ion-containing compound in a solvent (for example, halogen solvent, alcohol solvent, ether solvent, ester solvent, ketone solvent, nitrile solvent, amide solvent, sulfone solvent, sulfoxide solvent, or water) or in a solventless manner in the presence or absence of a base (an inorganic or an organic base such as sodium methoxide, potassium t-butoxide, triethylamine or potassium carbonate).

The compound of the invention can be synthesized, for example, with reference to a process as described in *Synthesis*, 5, 409-411 (1986) by reacting a corresponding dicarbonyl compound with hydrazine hydrate into a phenylpyrazole compound, reacting the resulting compound with an alkyl halide or phosgene to synthesize the corresponding ligand, and then reacting the organic ligand thus obtained with an appropriate platinum source as described above in the above-described solvent. The synthesis process is however not limited to it.

Although the reaction time required for synthesis of the compound of the invention differs, depending on the reaction activity and is therefore not particularly limited, it is preferably 1 minute or greater and not greater than 5 days, more preferably 5 minutes or greater and not greater than 3 days, more preferably 10 minutes or greater and not greater than 24 hours.

Although the reaction temperature for the synthesis of the compound of the invention differs, depending on the reaction activity and is therefore not particularly limited, it is preferably 0° C. or greater and not greater than 300° C., more preferably 5° C. or greater and not greater than 250° C., still more preferably 10° C. or greater and not greater than 230° C.

The compound of the invention can be synthesized by adding, to a platinum compound, a ligand constituting a partial structure of the intended complex in an amount of preferably from 0.1 to 10 equivalents, more preferably from 0.3 to 6 equivalents, still more preferably from 0.5 to 4 equivalents. Examples of the platinum compound include halides (for example, platinum chloride and potassium chloroplatinate), carboxylates (for example, platinum acetate), diketonates (for example, platinum acetylacetonate), platinum compounds containing an organic ligand (for example, dichlorocyclooctadienyl platinum), and hydrates thereof.

The following are specific examples of the compound of the invention but the invention is not limited to them.

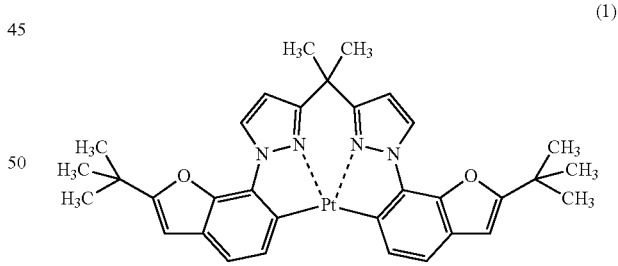

(1)

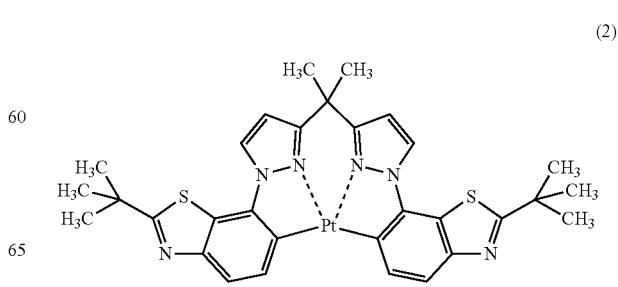

(2)

-continued
(3)
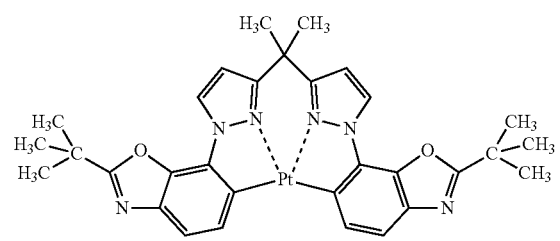
(4)
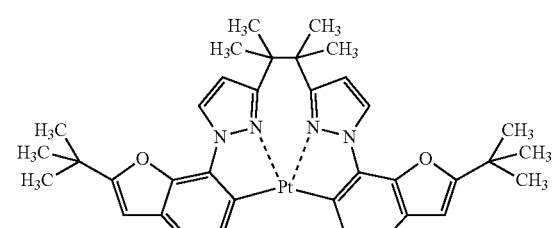
(5)
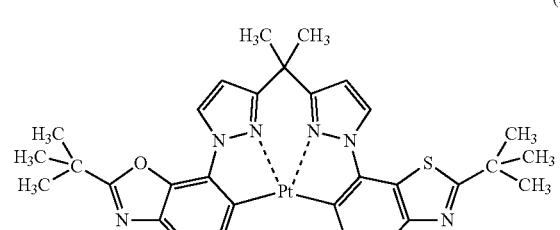
(6)
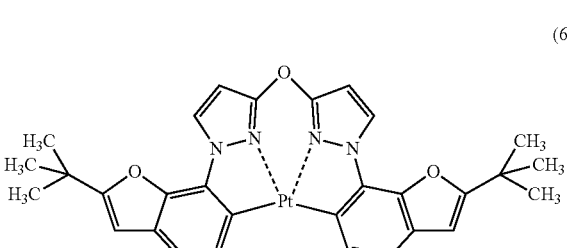
(7)
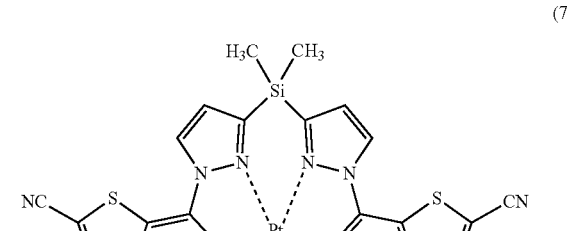
(8)
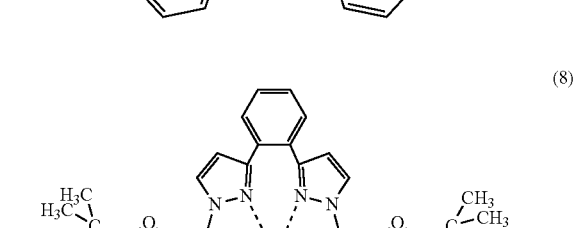
-continued
(9)
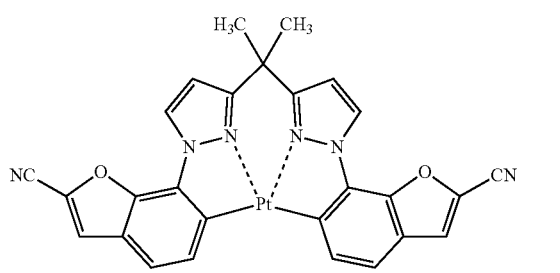
(10)
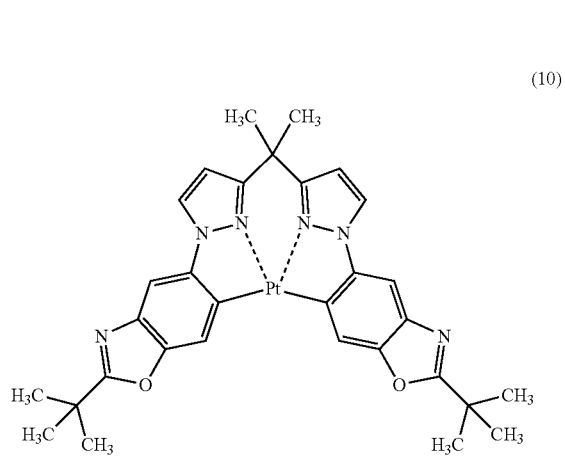
(11)
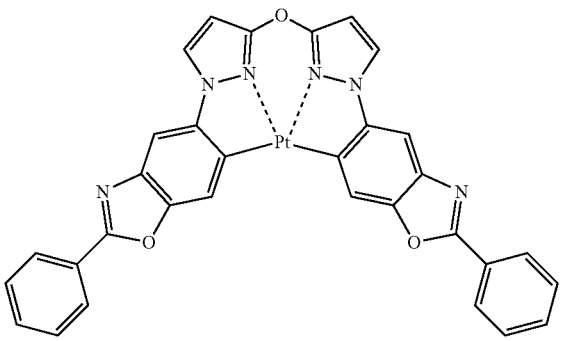
(12)
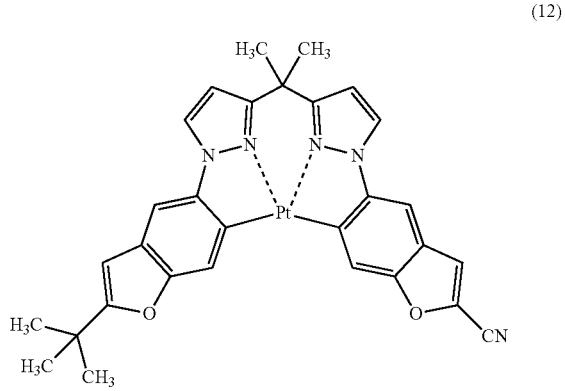

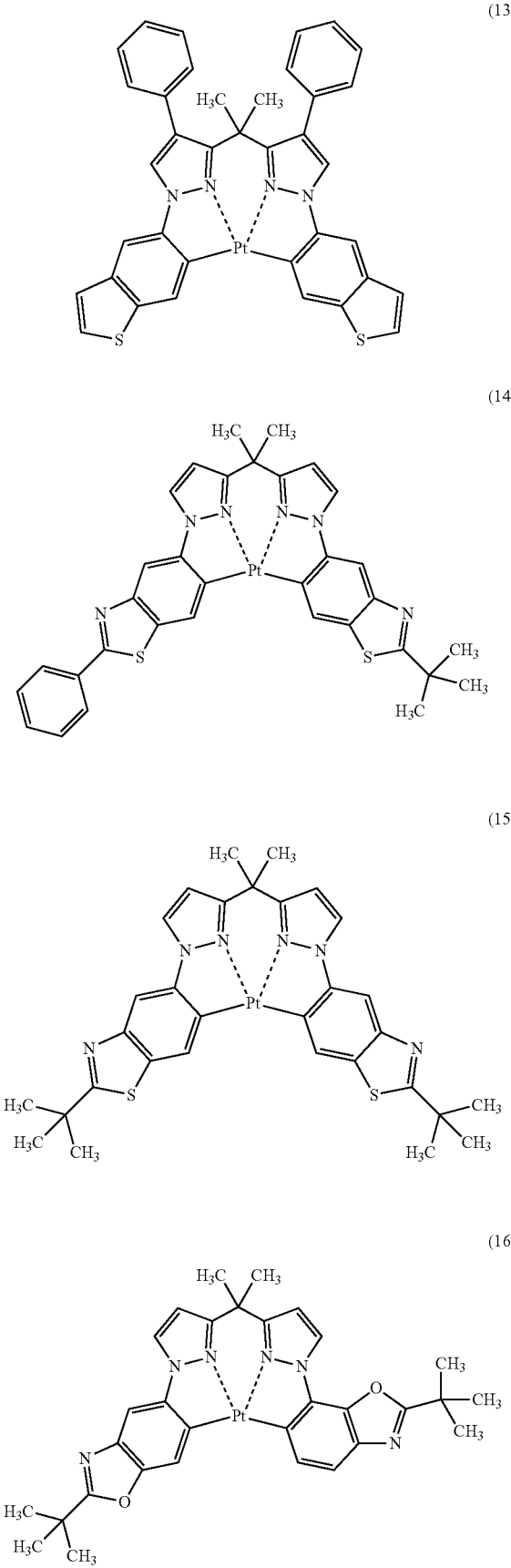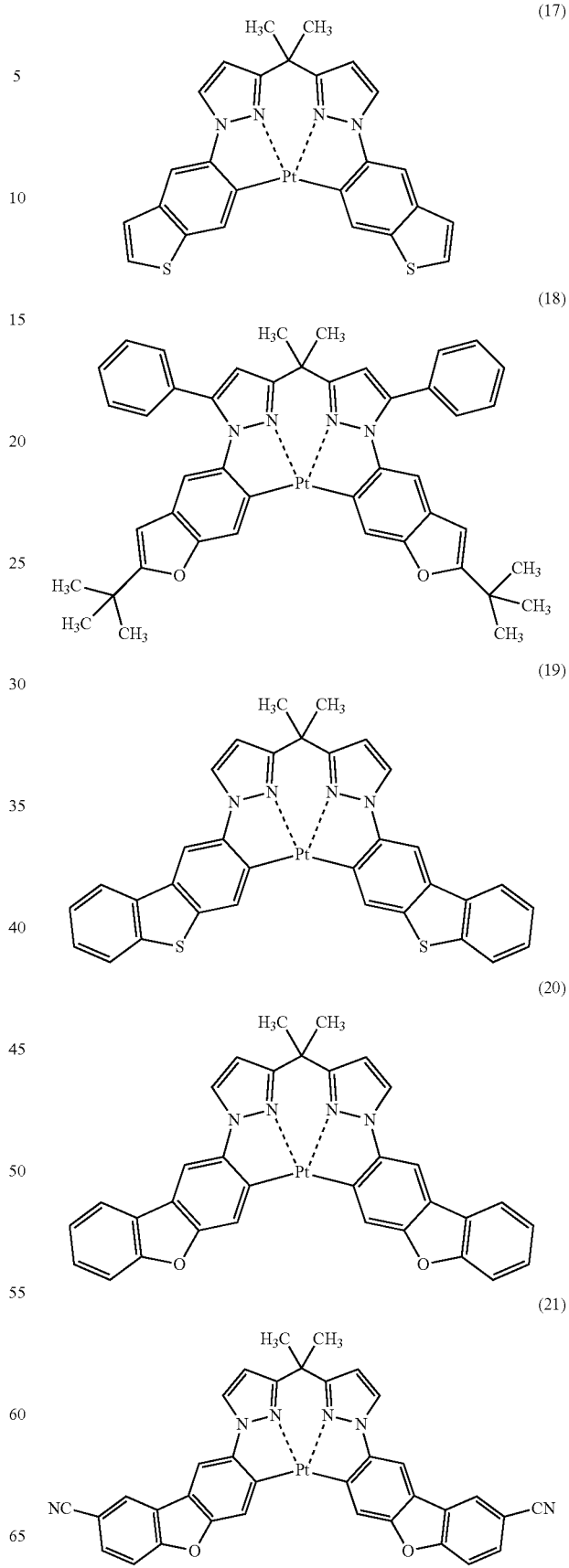

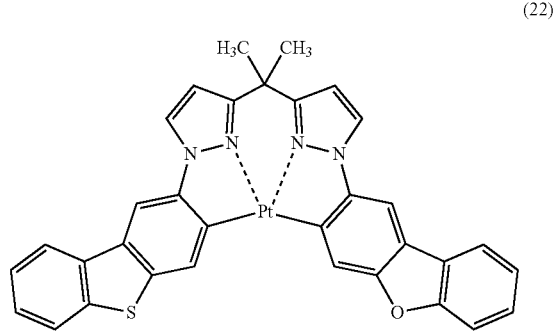
(22)
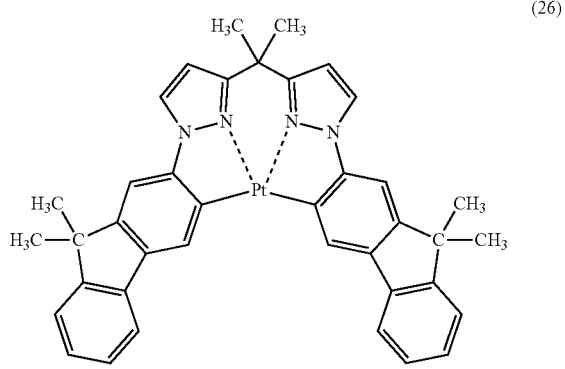
(26)
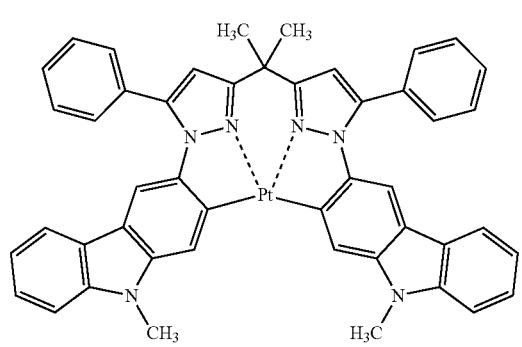
(23)
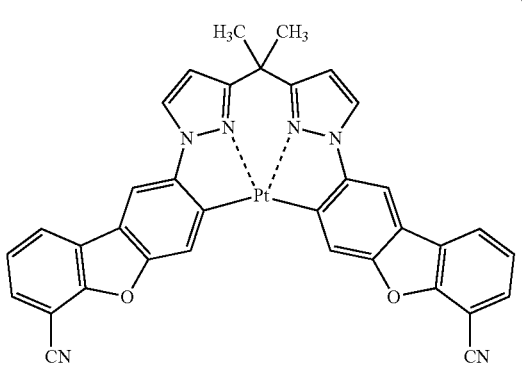
(27)
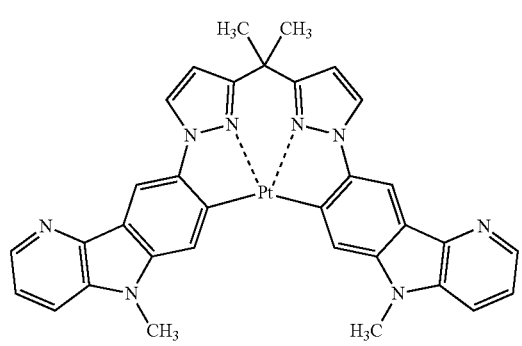
(24)
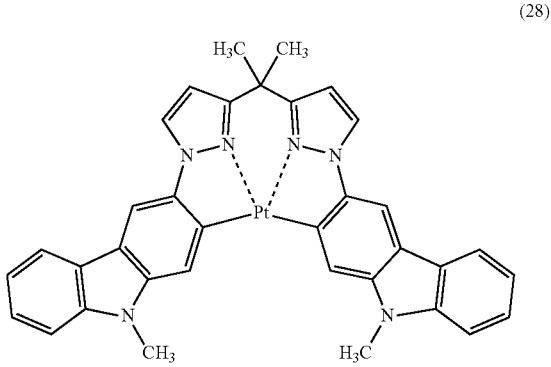
(28)
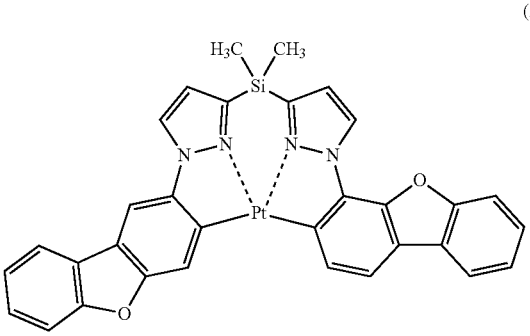
(25)
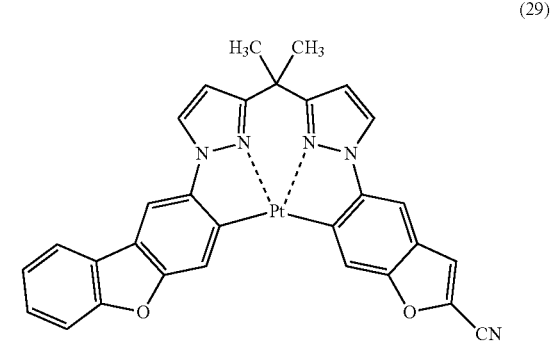
(29)

(30)
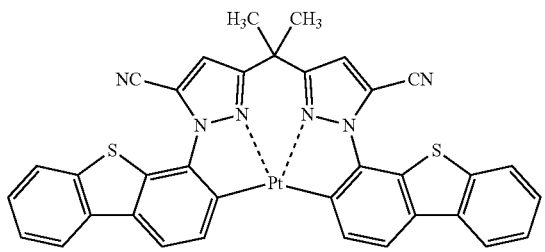
(31)
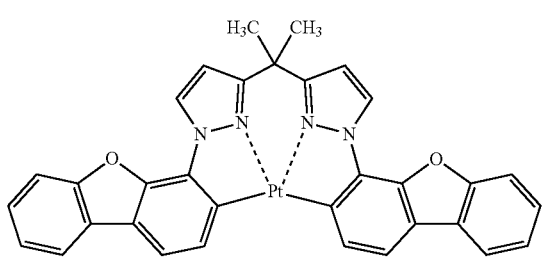
(32)
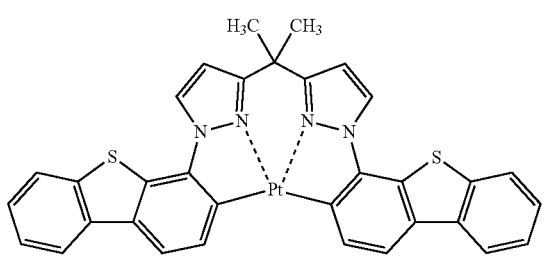
(33)
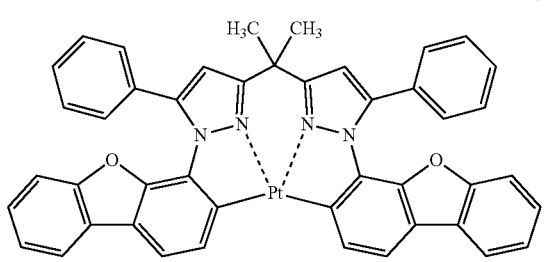
(34)
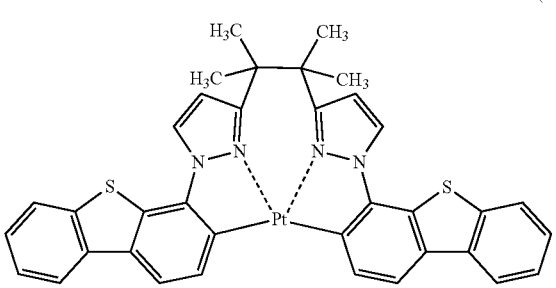
(35)
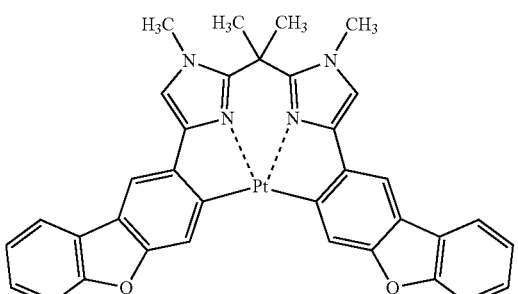
(36)
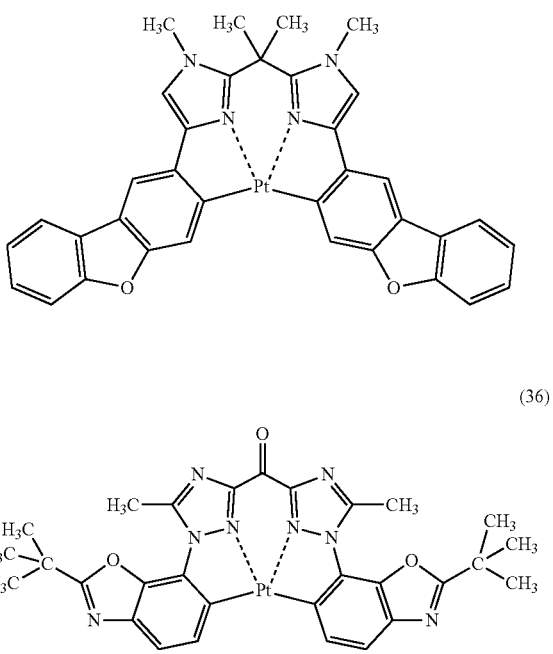
(37)
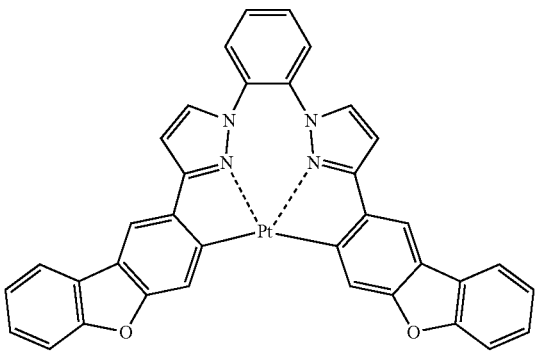
(38)
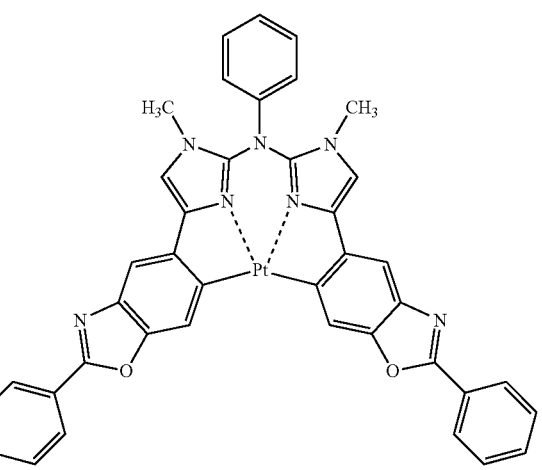

-continued
(39)
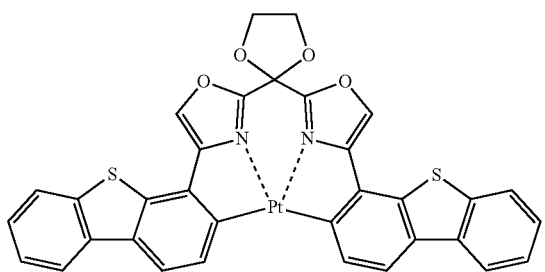
(40)
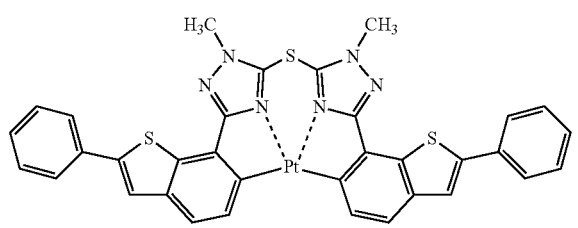
(41)
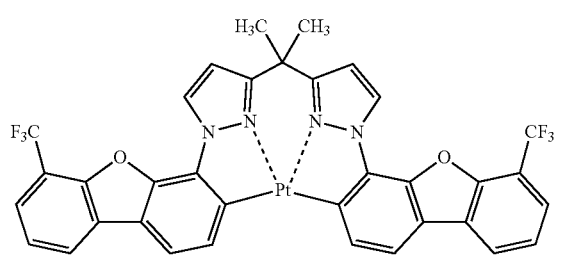
(42)
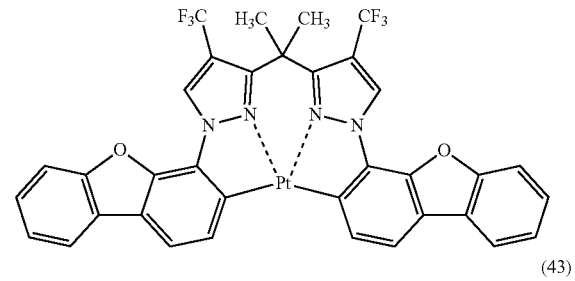
(43)
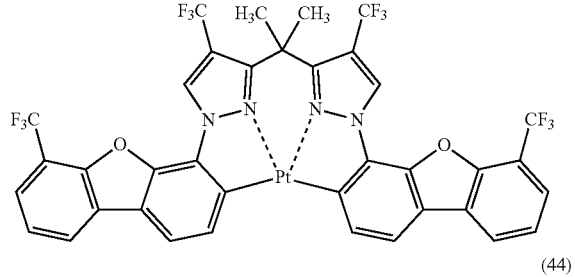
(44)
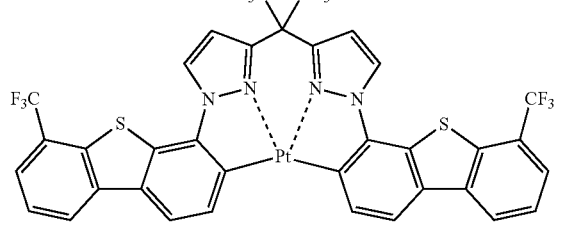
-continued
(45)
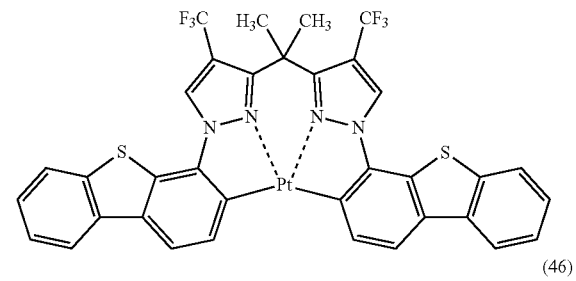
(46)
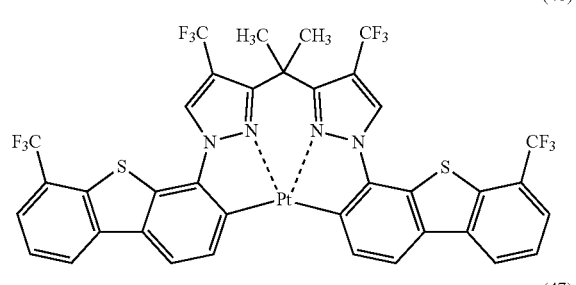
(47)
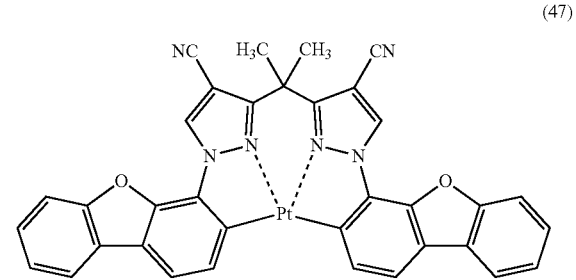
(48)
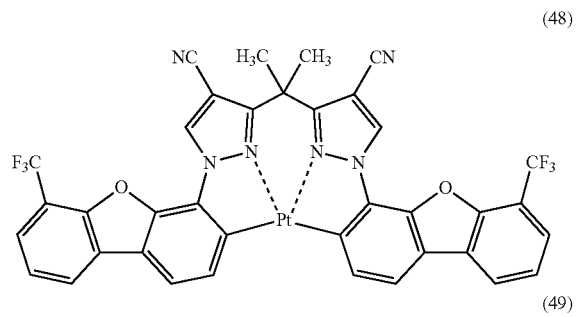
(49)
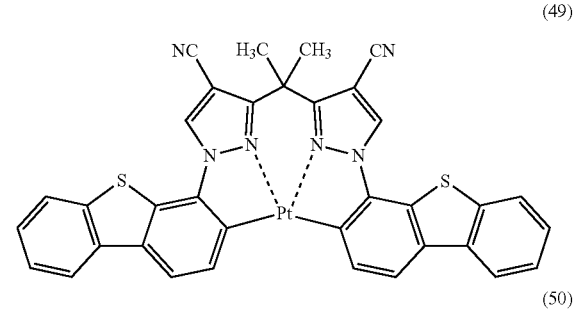
(50)
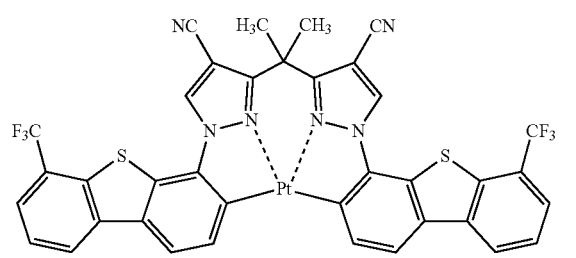

(51) 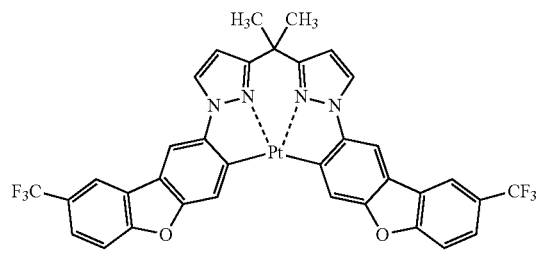
(52) 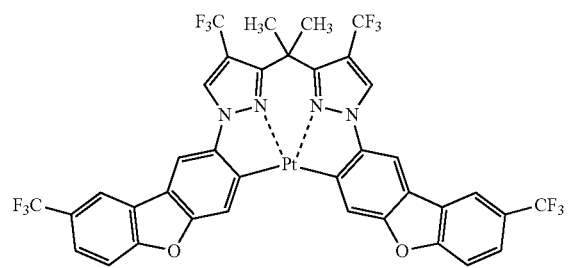
(53) 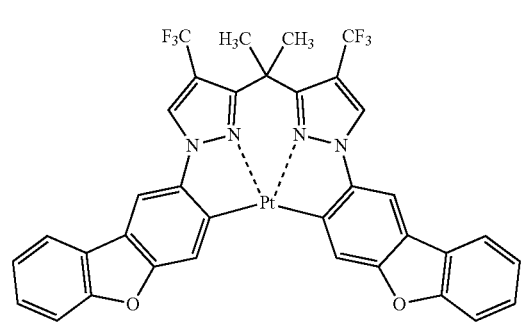
(54) 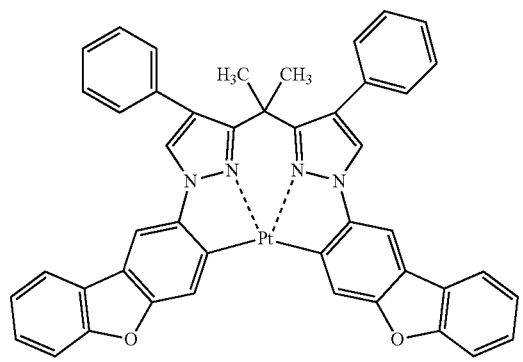
(55) 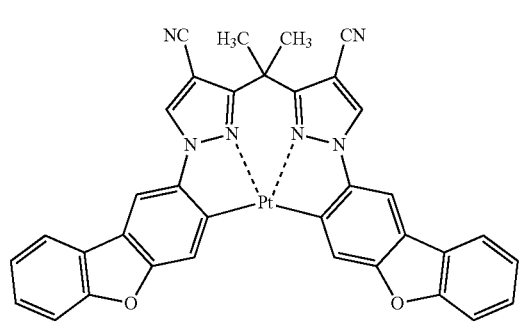
(56) 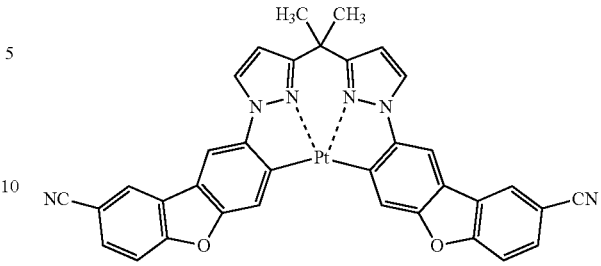
(57) 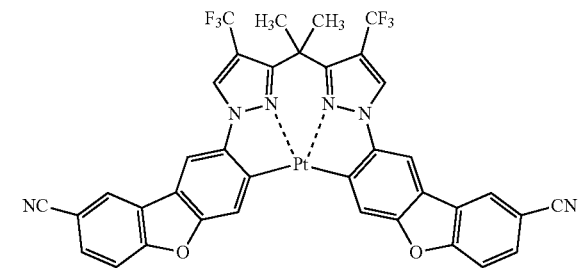
(58) 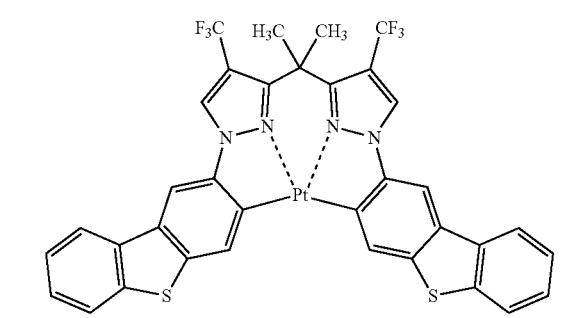
(59) 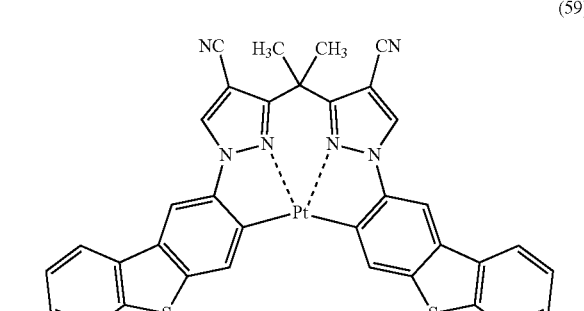
(60) 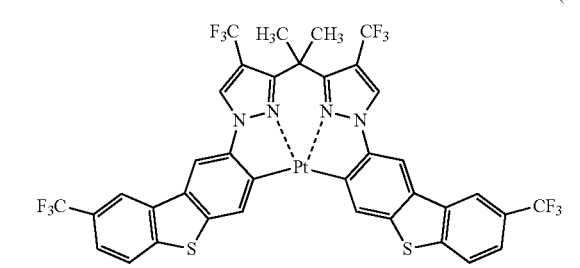
<Organic Electroluminescence Device>
The organic electroluminescence device according to the invention is described in detail. The device according to the invention is an organic electroluminescence device having a pair of electrodes and one or more organic layers, and the compound of the invention is incorporated into at least one of the organic layers. For instance, the device according to the invention has a negative electrode and a positive electrode on a substrate, and it has at least one organic layer (a light emitting layer when the device has only one organic layer) between both the electrodes. In view of properties of an electroluminescence device, it is preferred that at least one electrode of negative and positive electrodes be transparent.

In the device of the invention, the function of the one or more organic layers is not particularly limited but it may be, as well as a light emitting layer, a hole injection layer, a hole transport layer, an electron injection layer, an electron transport layer, a hole blocking layer, an electron blocking layer, an exciton blocking layer or a protective layer. In the device of the invention, the at lease one organic layer may have a hole injection layer, a hole transport layer, an electron injection layer, an electron transport layer, a hole blocking layer, an electron blocking layer, an exciton blocking layer or a protective layer, in addition to the light emitting layer. These layers may have another function simultaneously.

As a preferable stack mode of the organic layers in the invention, a hole transport layer, a light emitting layer, and an electron transport layer are stacked successively from the side of the anode. Further, the device has a charge blocking layer between the hole transport layer and the light emitting layer or between the light emitting layer and the electron transport layer. The device may have a hole injection layer between the anode and the hole transport layer. It may have an electron injection layer between the cathode and the electron transport layer. Each layer may be divided into a plurality of secondary layers.

<Substrate>

The substrate to be used in the invention preferably does not scatter or attenuate light emitted from the organic layers. Specific examples include inorganic materials such as yttria-stabilized zirconia (YSZ) and glass; and organic materials, e.g., polyesters such as polyethylene terephthalate, polybutylene terephthalate, and polyethylene naphthalate, polystyrenes, polycarbonates, polyethersulfones, polyarylates, polyimides, polycycloolefins, norbornene resins, and poly(chlorotrifluoro ethylene).

When glass is used as the substrate, use of an alkali-free glass is preferred in order to minimize elution of ions from the glass. When soda lime glass is used, a barrier coated one with, for example, silica is preferred. Substrates made of the organic materials are preferred because they are excellent in heat resistance, dimensional stability, solvent resistance, electrical insulating properties, and pro cessability.

The shape, structure, and size of the substrate are not particularly limited and can be selected as needed according to the intended use or purpose of the luminescence device. In general, the substrate is preferably in the form of a plate and may have either a single layer structure or a stacked structure. It may be made of a single member or two or more members.

Although the substrate may be either colorless and transparent or colored and transparent, a colorless and transparent substrate is preferred because such a substrate causes neither scattering nor attenuation of light emitted from the organic light emitting layer.

The substrate can have, on the surface or backside surface thereof, a moisture penetration preventing layer (gas barrier layer). As materials for the moisture penetration preventing layer (gas barrier layer), inorganic substances such as silicon nitride and silicon oxide are suited. The moisture penetration preventing layer (gas barrier layer) can be formed, for example, by RF sputtering.

When a thermoplastic substrate is used, it may have a hard coat layer or an undercoat layer further if necessary.

<Anode>

The anode is usually not particularly limited in shape, structure, or size insofar as it has a function as an electrode supplying holes to the organic layers. Materials of the anode can be selected as needed from known electrode materials, depending on the intended use or purpose of the luminescence device. As described above, the anode is usually formed as a transparent anode.

Examples of the materials of the anode include metals, alloys, metal oxides, and electroconductive compounds, and mixtures thereof. Specific examples of the anode material include electroconductive metal oxides such as tin oxides doped with antimony and fluorine (e.g., ATO and FTO), tin oxide, zinc oxide, indium oxide, indium tin oxide (ITO) and indium zinc oxide (IZO), metals such as gold, silver, chromium, and nickel, mixtures or stacks of these metals and electroconductive metal oxides; inorganic electroconductive substances such as copper iodide and copper sulfide, organic electroconductive materials such as polyaniline, polythiophene, and polypyrrole; and stacks of these materials with ITO. Among these materials, electro conductive metal oxides are preferred, with ITO being especially preferred from the viewpoint of productivity, and high conductivity, transparency.

The anode can be formed over the substrate by a process selected as needed from the wet processes such as printing and coating, physical processes such as vacuum deposition, sputtering and ion plating, and chemical processes such as CVD and plasma CVD in consideration of its suitability to the material constituting the anode. When ITO is selected as the anode material, the anode can be formed by DC sputtering, RF sputtering, vacuum deposition, or ion plating.

In the device of the invention, the formation position of the anode is not particularly limited and it can be selected as needed depending on the intended use or purpose of the luminescence device. It is however preferably formed on the substrate. In this case, the anode may be formed all over the one surface of the substrate or may be formed in a part thereof.

When the anode is formed, patterning may be performed by chemical etching using photolithography or physical etching with laser exposure. The anode may also be formed by vacuum deposition or sputtering through stacked masks, a lift-off process, or a printing process.

Although the thickness of the anode can be selected as needed, depending on the material constituting the anode and it cannot be specified in a wholesale manner, the thickness is usually from approximately 10 nm to 50 µm, preferably from 50 nm to 20 µm.

The resistivity of the anode is preferably $10^3$ Ω/sq or less, more preferably $10^2$ Ω/sq. The anode may be either colorless or colored insofar as it is transparent. The transmittance of the anode is preferably 60% or greater, more preferably 70% or greater in order to obtain luminescence from the side of the transparent anode.

Detailed description on transparent anodes is given in *Development of Transparent Conductive Films*, supervised by Yutaka Sawada, published by CMC (1999) and it can be applied to the invention. When a plastic base material having low heat resistance is used, a transparent anode formed using ITO or IZO at a temperature as low as 150° C. or less is preferred.

<Cathode>

The shape, structure or size of the cathode is usually not particularly limited insofar as it has a function as an electrode charging electrons into the organic layers. The material of it can be selected as needed from known electrode materials, depending on the intended use or purpose of the device.

Materials making up the cathode are, for example, metals, alloys, metal oxides, and electroconductive compounds, and mixtures thereof. Specific examples include alkali metals (such as Li, Na, K, and Cs), alkaline earth metals (such as Mg and Ca), gold, silver, lead, aluminum, sodium-potassium alloy, lithium-aluminum alloy, magnesium-silver alloy, and rare earth metals such as indium and ytterbium. These materials may be used alone. From the viewpoint of satisfying both stability and electron injection property, however, two or more of them can be used preferably in combination.

Of these, alkali metals and alkaline earth metals are preferred as the material constituting the cathode from the viewpoint of electron injection property, while materials composed mainly of aluminum are preferred because of their excellent storage stability.

The term "materials composed mainly of aluminum" means a single substance of aluminum and mixtures or alloys composed of aluminum and from 0.01 to 10 mass % of an alkali metal or an alkaline earth metal (such as a lithium-aluminum alloy and a magnesium-aluminum alloy).

The materials of the cathode are described in detail in JP-A-2-15595 and JP-A-5-121172 and the materials described therein can also be employed in the invention.

The process of forming the cathode is not particularly limited and it can be formed in a known manner. It can be formed in accordance with a process selected as needed from wet processes such as printing and coating, physical processes such as vacuum deposition, sputtering and ion plating, and chemical processes such as CVD and plasma CVD in consideration of the suitability to the above-described material making up the cathode. When a metal is selected as the material for the cathode, the cathode may be formed by simultaneously or successively sputtering one or more of the metals.

When the cathode is formed, patterning may be performed by chemical etching using photolithography or physical etching with laser exposure. The cathode may also be formed by vacuum deposition or sputtering through stacked masks, or by a lift-off process or a printing process.

In the invention, the forming position of the cathode is not particularly limited and it may be formed all over the organic layer or may be formed over a part thereof.

A dielectric layer made of, for example, a fluoride or oxide of an alkali metal or an alkaline earth metal and having a thickness of from 0.1 nm to 5 nm may be inserted between the cathode and the organic layer. This dielectric layer can also be regarded as a kind of an electron injection layer. It may be formed, for example, by vacuum deposition, sputtering or ion plating.

The thickness of the cathode can be selected as needed, depending on the material constituting the cathode and it cannot be determined in a wholesale manner. The thickness is usually from 10 nm to 5 μm, preferably from 50 nm to 1 μm.

The cathode may be either transparent or opaque. A transparent cathode can be obtained by forming the material of the cathode into a thin film with a thickness of from 1 to 10 nm and then stacking thereover a transparent conductive material such as ITO or IZO.

<Organic Layer>

The organic layer in the invention will next be described. The organic layer may be a layer composed only of an organic compound or may be a layer containing both an organic compound and an inorganic compound.

The organic electroluminescence device of the invention has one or more organic layers including a light emitting layer and it contains at least one light emitting layer. Examples of the organic layer other than the light emitting layer include, as described above, a hole transport layer, an electron transport layer, a charge blocking layer, a hole injection layer, and an electron injection layer.

—Formation of Organic Layer—

In the organic electroluminescence device of the invention, each layer of the organic layer can be formed preferably by any of dry film formation processes such as vapor deposition or sputtering, transfer process, and printing process.

—Light Emitting Layer—

The light emitting layer is a layer having a function of when voltage is applied, receiving holes from the anode, the hole injection layer, or the hole transport layer, receiving electrons from the cathode, the electron injection layer, or the electron transport layer, and providing a recombination site of the holes and electrons to cause light emission.

In the invention, the light emitting layer may be composed of a light emitting material alone, or it may be configured as a mixed layer of a host material and a light-emitting material. The light emitting material may be composed of the present compound alone, or it may be a combination of the present compound and a fluorescence- or phosphorescence-producing material other than the present compound. And only one or at least two kinds of dopants (compounds included in the light emitting material) may be used. The host material is preferably a charge transport material. As to the kind thereof, only one kind of host material may be used, or two or more kinds of host materials may be used in combination. For instance, a mixed composition of an electron-transportable host material and a hole-transportable host material may be used. Further, a material which has no capability of transporting charge and gives off no light emission may be incorporated into the light emitting layer.

The light emitting layer may be either a single layer or two or more layers. When it has two or more layers, they may emit lights of different colors, respectively.

Examples of the fluorescent material usable in combination with the compound of the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, fused aromatic compounds, perynone derivatives, oxadiazole derivatives, oxazine derivatives, aldazine derivatives, pyralidine derivatives, cyclopentadiene derivatives, bis-styrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, various metal complexes as typified by metal complexes of 8-quinolynol and metal complexes of a pyromethene derivatives, polymer compounds such as polythiophene, polyphenylene, and polyphenylene vinylene, and compounds such as organosilane derivatives.

When a fluorescence material is used, the content of the fluorescence material in the light emitting layer is preferably from 0.1 to 10 mass %, more preferably from 0.2 to 5 mass %, still more preferably from 0.5 to 2 mass %.

Examples of the phosphorescent material to be used in combination with the compound of the invention include complexes containing a transition metal atom or a lanthanoid atom. Preferred examples of the transition metal atom include, but not limited particularly to, ruthenium, rhodium, palladium, tungsten, rhenium, osmium, iridium, gold, silver, copper, and platinum. Of these, rhenium, iridium, and platinum are more preferred, with iridium and platinum being still more preferred. Examples of the lanthanoid atom include lanthanum, cerium, praseodymium, neodymium, samarium, europium, gadolinium, terbium, dysprosium, holmium, erbium, thulium, ytterbium, and lutecium. Of these, neodium, europium, and gadolinium are preferred.

As the ligand of the complex, ligands described in, for example, G Wilkinson et al., *Comprehensive Coordination Chemistry*, published by Pergamon Press in 1987; H. Yersin, *Photochemistry and Photophysics of Coordination Compounds*, published by Springer-Verlag in 1987; and Akio Yamamoto, *Organometallic Chemistry-Principles and Applications*, published by Shokabo Publishing in 1982, can be used.

Specific examples of the ligands include preferably halogen ligands (preferably chlorine ligand), nitrogen-containing heterocyclic ligands (such as phenylpyridine, benzoquinoline, quinolinol, bipyridyl, and phenanthroline), diketone ligands (such as acetylacetone), carboxylic acid ligands (such as acetic acid ligand), a carbon monoxide ligand, an isonitrile ligand, and a cyano ligand. Of these, the nitrogen-containing heterocyclic ligands are more preferred. The above-described complexes may be either a complex containing one transition metal atom in the compound, or a so-called polynuclear complex containing two or more transition metal atoms. They may contain different metal atoms at the same time.

Of these, specific examples of the phosphorescent material include, in addition to the compound of the invention, phosphorescent compounds described in patent documents such as U.S. Pat. Nos. 6,303,238B1 and 6,097,147, WO 00/57676, 00/70655, 01/08230, 01/39234A2, 01/41512A1, 02/02714A2, 02/15645A1, 02/44189A1, and 05/19373A2, and JP-A-2001-247859, JP-A-2002-302671, JP-A-2002-117978, JP-A-2003-133074, JP-A-2002-235076, JP-A-2003-123982, and JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Of these, more preferred examples of the luminescent dopant include Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, of which Ir complexes, Pt complexes, and Re complexes are especially preferred. Of these, Ir complexes, Pt complexes, and Re complexes each containing at least one coordination mode of metal-carbon bonds, metal-nitrogen bonds, metal-oxygen bonds, and metal-sulfur bonds are preferred. Furthermore, from the standpoint of luminous efficiency, running durability, and chromaticity, Ir complexes, Pt complexes and Re complexes each containing a tridentate or higher-dentate ligand are especially preferred.

The phosphorescent material is contained in the light emitting layer preferably in an amount of from 0.1 to 50 mass %, more preferably from 1 to 50 mass %, still more preferably from 2 to 40 mass %.

As the host material to be contained in the light emitting layer in the invention, materials having a $T_1$ level, in the form of a single film, falling within the above-described range. Examples include materials having a carbazole skeleton, those having a diarylamine skeleton, those having a pyridine skeleton, those having a pyrazine skeleton, those having a triazine skeleton, those having an arylsilane skeleton, and those exemplified later in the description of the hole injection layer, the hole transport layer, the electron injection layer, or the electron transport layer.

Although the thickness of the light emitting layer is not particularly limited, typically it is preferably from 1 to 500 nm, more preferably from 5 to 200 nm, still more preferably from 10 to 100 nm.

In the organic electroluminescence device according to the invention, it is preferable that the at least one organic layer includes a light emitting layer and the light emitting layer contains the compound of the invention and a host material which has a $T_1$ level of 61 kcal/mol or greater in the form of a single layer. By having such a makeup, the invention can achieve an increase of the external quantum efficiency and the luminance half-life.

—Hole Injection Layer, Hole Transport Layer—

A hole injection layer and a hole transport layer each has a function of receiving holes from the anode or anode side and transporting them to the cathode side.

Specifically, the hole injection layer and the hole transport layer are preferably layers containing a carbazole derivative, a triazole derivative, an oxazole derivative, an oxadiazole derivative, an imidazole derivative, a polyarylalkane derivative, a pyrazoline derivative, a pyrazolon derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, a porphyrine compound, an organic silane derivative, or a carbon.

The thickness of each of the hole injection layer and the hole transport layer is preferably 500 nm or less in order to reduce the driving voltage.

The thickness of the hole transport layer is preferably from 1 to 500 nm, more preferably from 5 nm to 200 nm, still more preferably from 10 nm to 100 nm. The thickness of the hole injection layer is preferably from 0.1 nm to 200 nm, more preferably from 0.5 to 100 nm, still more preferably from 1 to 100 nm.

The transport injection layer and the hole transport layer may each be a single layer composed of one or more of the above-described materials or a multilayer composed of a plurality of layers having the same composition or different compositions.

—Electron Injection Layer, Electron Transport Layer—

The electron injection layer and the electron transport layer are layers having a function of receiving electrons from the cathode or the cathode side and transporting them to the anode side.

Specifically, the electron injection layer and the electron transport layer are preferably layers containing a triazole derivative, an oxazole derivative, an oxadiazole derivative, an imidazole derivative, a fluorenone derivative, an anthraquinodimethane derivative, an anthrone derivative, a diphenylquinone deriative, a thiopyran dioxide derivative, a carbodiimide derivative, a fluorenylidenemethane derivative, a distyrylpyrazine derivative, an aromatic cyclic tetracarboxylic anhydride such as naphthalene and perylene, various complexes typified by a metal complex of a 8-quinolinol derivative, metalphthalocyanines, and metal complexes having benzoxazole or benzothiazole as a ligand, and organic silane derivatives.

The thickness of each of the electron injection layer and the electron transport layer is preferably 50 nm or less in order to reduce the driving voltage.

The thickness of the electron transport layer is preferably from 1 to 500 nm, more preferably from 5 nm to 200 nm, still more preferably from 10 nm to 100 nm. The thickness of the electron injection layer is preferably from 0.1 to 200 nm, more preferably from 0.2 to 100 nm, still more preferably from 0.5 to 50 nm.

Each of the electron injection layer and the electron transport layer may be a single layer composed of one or more of the above-described materials or a multilayer composed of a plurality of layers having the same composition or having different compositions.

—Hole Blocking Layer—

The hole blocking layer is a layer having a function of preventing passage of holes, which have been transported to the light emitting layer from the anode side, to the cathode side. In the invention, the hole blocking layer can be formed as an organic layer adjacent to the light emitting layer on the cathode side.

Examples of an organic compound included in the hole blocking layer include an aluminum complex such as aluminum(III) bis(2-methyl-8-quinolinato)-4-phenylphenolate (abbreviated as "BAlq"), a triazole derivative, and a phenanthro line derivative such as 2,9-dimethyl-4,7-diphenyl-1,10-phenanthroline (abbreviated as "BCP"). The thickness of the hole blocking layer is preferably from 1 nm to 500 nm, more preferably from 5 nm to 200 nm, still more preferably from 10 nm to 100 nm.

The hole blocking layer may be a single layer composed of one or more of the above-described materials or a multilayer composed of a plurality of layers having the same composition or different compositions.

<Protective Layer>

In the invention, the whole organic EL device may be protected by a protective layer.

Any material may be incorporated in the protective layer insofar as it has a function of preventing intrusion of substances, which promote deterioration of the device such as water or oxygen, into the device.

Specific examples of the material include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$, and $TiO_2$; metal nitrides such as $SiN_x$ and $SiN_xO_y$; metal fluorides such as $MgF_2$, LiF, $AlF_3$ and $CaF_2$; polyethylene, polypropylene, poly(methyl methacrylate), polyimide, polyurea, polytetrafluoroethylene, polychlorotrifluoroethylene, polydichlorodifluoroethylene, chlorotrifluoro ethylene/dichloro difluoro ethylene copolymer, copolymers obtainable by copolymerizing a monomer mixture containing tetrafluoroethylene and at least one comonomer, fluorine-containing copolymers having, on the copolymer backbone thereof, a ring structure, water absorptive materials having a water absorption of 1% or greater, and moisture-proof materials having a water absorption of 0.1% or less.

A process for forming the protective layer is not particularly limited. Examples of the process applicable to the formation include a vacuum deposition process, a sputtering process, a reactive sputtering process, a MBE (molecular beam epitaxy) process, a cluster ion beam process, an ion plating process, a plasma polymerization process (high-frequency excited ion plating process), a plasma CVD process, a laser CVD process, a thermal CVD process, a gas source CVD process, a coating process, a printing process, and a transfer process.

<Sealing>

The entire organic electroluminescence device of the invention may be sealed using a sealing container.

Also, a space between the sealing container and the device may be filled with a moisture absorbent or an inert liquid. The moisture absorbent is not particularly limited. Examples of it include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, a molecular sieve, zeolite, and magnesium oxide. The inert liquid is not particularly limited and examples of it include paraffins, liquid paraffins, fluorine-based solvents such as perfluoroalkanes, perfluoroamines and perfluoroethers, chlorine-based solvents, and silicone oils.

By applying a direct current (which may contain an alternating current component if necessary) voltage (usually from 2 to 15V) or a direct current between the anode and the cathode of the organic electroluminescence device of the invention, light emission can be obtained.

Examples of a method for driving the organic electroluminescence device of the invention include those described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308.

EXAMPLES

The present invention will hereinafter be described specifically based on Examples. It should however be borne in mind that the embodiments of the invention are not limited to by them.

Exemplified Compounds (19), (20), (31), and (32), among the compounds of the invention represented by the formula (I), are synthesized, but the present invention is not limited to this synthesis process.

<Synthesis of Compound (31) of the Invention>

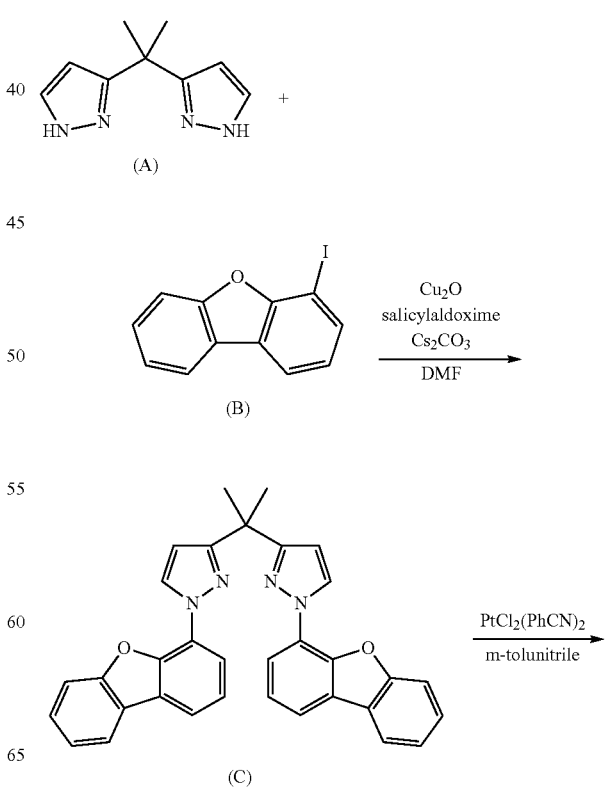

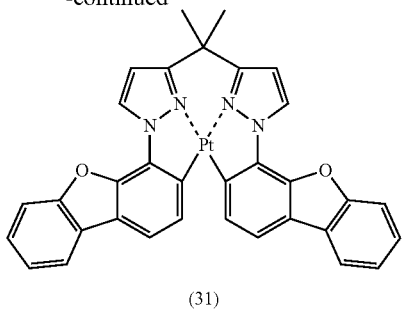

(31)

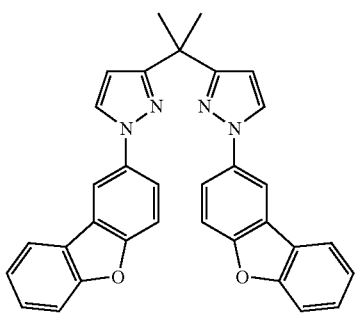

(E)

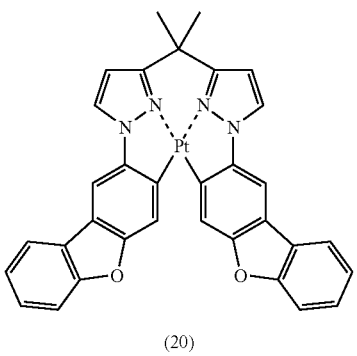

(20)

In a nitrogen atmosphere, 1.76 g (10 mmol) of Compound (A), 11.76 g (40 mmol) of 2-iododibenzofuran (B), 0.14 g (1 mmol) of copper oxide, 0.55 g (4 mmol) of salicylaldoxime, 13.0 g (40 mmol) of cesium carbonate, and 200 mL of DMF are charged in a 200-mL three-necked flask and the mixture is reacted at 150° C. for 16 hours. The reaction mixture is filtered and concentrated. The residue thus obtained is purified by silica gel chromatography (developing solvent: hexane/ethyl acetate=4/1) to yield 1.80 g of Compound (C). Yield: 35%.

$^1$H-NMR (300 MHz, in CDCl$_3$): δ (ppm)=8.59 (d, 2H), 8.19 (d, 2H), 8.0 (d, 2H), 7.83 (d, 2H), 7.64 (d, 2H), 7.52-7.37 (m, 6H), 6.48 (d, 2H), 1.94 (s, 6H).

In a nitrogen atmosphere 1.40 g (2 mmol) of Compound (C), 0.94 g (2 mmol) of bis(benzonitrile) platinum(II) chloride, and 40 mL of m-tolunitrile are charged in a 50-mL eggplant type flask. The resulting mixture is heated at 230° C. for 5 hours. After cooling to room temperature, 40 mL of hexane is added to the reaction mixture. A brown solid thus precipitated is purified by silica gel chromatography (developing solvent: chloroform) to yield 1.28 g of Compound (31). Yield: 91%. Exemplified compound (31) of the invention emits light at 480 nm at room temperature in a dichloromethane solution. A film obtained by co-deposition of Exemplified compound (31) and 1,3-bis(N-carbazolyl)benzene (MCP) has a PL emission quantum yield of 0.9.

$^1$H-NMR (300 MHz, in CDCl$_3$): δ (ppm)=8.75 (d, 2H), 8.20 (dd, 2H), 7.98 (d, 2H), 7.88 (d, 2H), 7.62 (d, 2H), 7.47 (t, 2H), 7.37 (t, 2H), 6.74 (d, 2H), 1.92 (s, 6H).

<Synthesis of Compound (20) of the Invention>

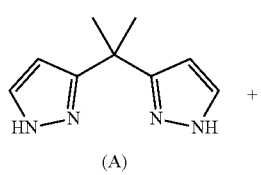

(A)

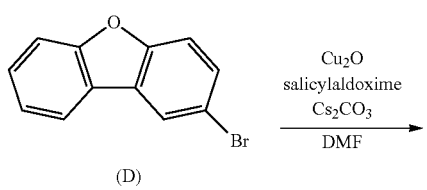

(D)

In a nitrogen atmosphere, 2.64 g (15 mmol) of Compound (A), 14.83 g (60 mmol) of 3-bromodibenzofuran (D), 0.22 g (1.5 mmol) of copper oxide, 0.83 g (6 mmol) of salicylaldoxime, 19.55 g (60 mmol) of cesium carbonate, and 50 mL of DMF are charged in a 200-mL three-necked flask and the mixture is reacted at 150° C. for 24 hours. The reaction mixture is filtered and concentrated. The residue thus obtained is purified by silica gel chromatography (developing solvent: hexane/ethyl acetate=4/1) to yield 2.1 g of Compound (E). Yield: 26%.

$^1$H-NMR (300 MHz, in CDCl$_3$): δ (ppm)=8.28 (d, 2H), 8.01 (d, 2H), 7.90 (s, 2H), 7.78 (d, 2H), 7.66-7.55 (m, 4H), 7.50 (t, 2H), 7.37 (t, 2H), 6.41 (d, 2H), 1.94 (s, 6H).

In a nitrogen atmosphere, 1.50 g (2.95 mmol) of Compound (E), 1.32 g (2.8 mmol) of bis(benzonitrile) platinum (II) chloride, and 45 mL of m-tolunitrile are charged in a 50-mL eggplant type flask and the resulting mixture is heated at 230° C. for 9 hours. After cooling to room temperature, 45 mL of hexane is added to the reaction mixture. A brown solid thus precipitated is purified by silica gel chromatography (developing solvent: chloroform) to yield 1.18 g of Compound (20). Yield: 56%. Exemplified Compound (20) of the invention emits light at 445 nm at room temperature in a dichloromethane solution. A film obtained by co-deposition of Exemplified Compound (20) and 1,3-bis(N-carbazolyl)benzene (MCP) has a PL emission quantum yield of 0.5.

$^1$H-NMR (400 MHz, in CDCl$_3$): δ (ppm)=8.39 (t, 2H), 8.09 (s, 2H), 7.9 (m, 4H), 7.62 (d, 2H), 7.46 (t, 2H), 7.33 (t, 2H), 6.64 (d, 2H), 1.86 (s, 6H).

<Synthesis of Compound (32) of the Invention>

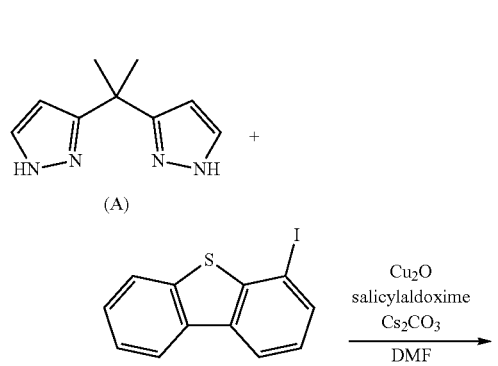

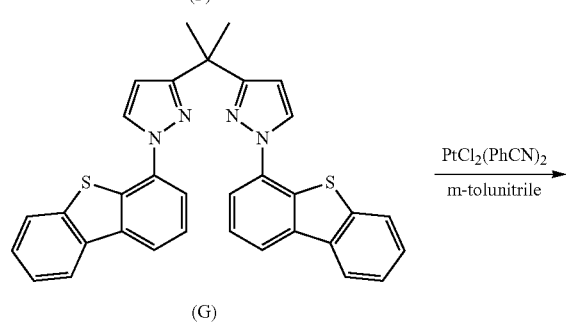

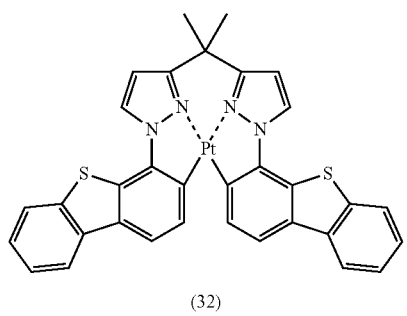

In a similar manner to that employed above while using Compound (A) and Compound (F) as starting materials, Compound (32) can be synthesized.

<Synthesis of Compound (19) of the Invention>

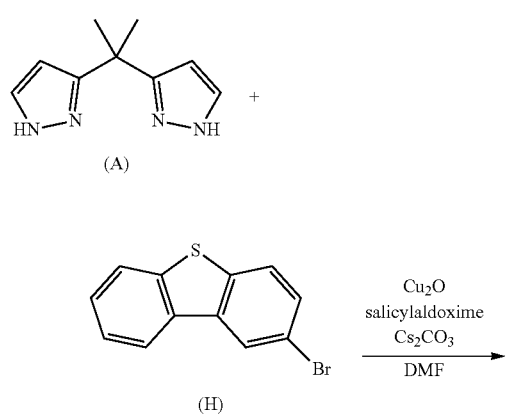

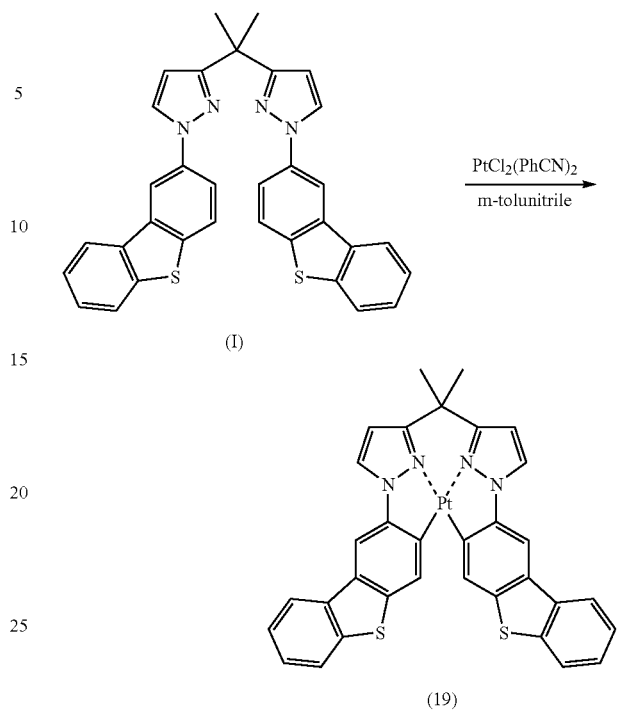

In a similar manner to that employed above while using Compound (A) and Compound (H) as starting materials, Compound (19) can be synthesized.

The chemical structures of other compounds used in Comparative Examples and Examples are shown below.

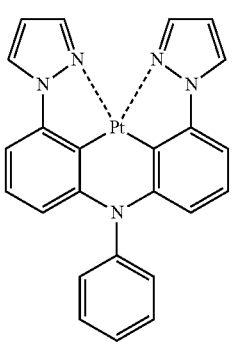

Comparative compound (1)

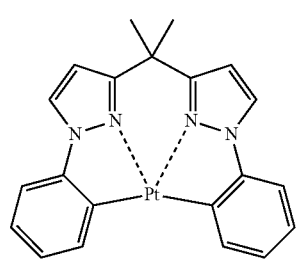

Comparative compound (2)

-continued

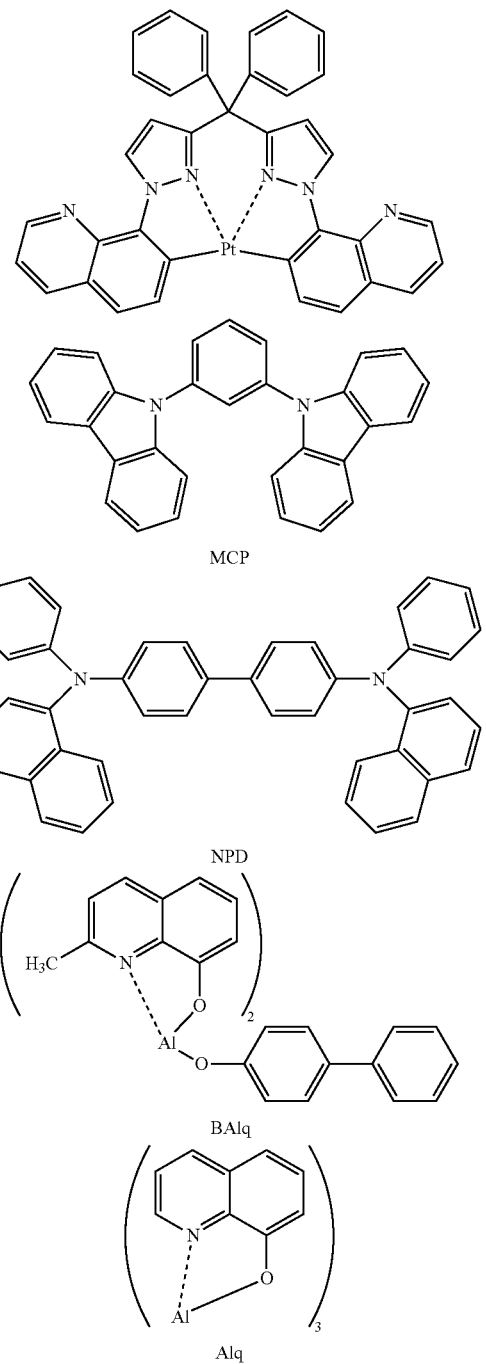

Comparative compound (3)

MCP

NPD

BAlq

Alq

Comparative Example 1

A glass substrate (product of Geomatec having a surface resistivity of 10 Ω/sq) which is 0.5 mm thick and 2.5 cm square and has an ITO film thereon is put in a cleaning container, ultrasonically cleaned in 2-propanol, and treated with UV ozone for 30 minutes. On the resulting transparent anode (ITO film), following organic layers are deposited successively by vacuum deposition.

A deposition rate in Examples of the invention is 0.2 nm/sec unless otherwise particularly specified. The deposition rate is measured using a crystal oscillator. Film thicknesses described below are also measured using a crystal oscillator.

The cleaned ITO substrate is put in a deposition apparatus. After vapor deposition of NPD to a thickness of 50 nm, MCP ($T_1$ level in the form of a single layer): 67 kcal/mol) and Comparative compound (1) (Compound described in JP-A-2006-232784: emission wavelength: 491 nm) are vapor deposited over the NPD film at a mass ratio of 10:1 to give a thickness of 60 nm, followed by vapor deposition thereover 10 nm of BAlq and 30 nm of Alq. A patterned mask (to make an emission area of 4 mm×5 mm) is placed over the resulting organic films. After vapor deposition of lithium fluoride to a thickness of 3 nm, aluminum is vapor deposited to a thickness of 60 nm. Without bringing it into contact with the atmosphere, the product is put in a glove box replaced with an argon gas and sealed in a sealing can made of stainless with a UV-curing adhesive ("XNR5516HV", product of Nagase Ciba) to obtain the Comparative Example 1. When a DC constant voltage (7V) is applied to the organic EL device thus fabricated, bluish green light emission is observed.

Comparative Example 2

In a similar manner to Comparative Example 1 except for the use of Comparative Compound (2) (the compound described in JP-A-2007-96255, emission wavelength: 460 nm) instead of Comparative Compound 1, an organic EL device of Comparative Example 2 is fabricated. When a DC constant voltage (7V) is applied to the resulting organic EL device, blue light emission is observed.

Comparative Example 3

In a similar manner to Comparative Example 1 except for the use of Comparative Compound (3) (the compound described in JP-A-2007-96255, emission wavelength: 540 nm) instead of Comparative compound 1, an organic EL device of Comparative Example 3 is fabricated. When a DC constant voltage (7V) is applied to the resulting organic EL device, yellowish green emission is observed.

Example 1

In a similar manner to Comparative Example 1 except for the use of Compound (31) of the invention (emission wavelength: 480 nm) instead of Comparative compound 1, an organic EL device of Example 1 is fabricated. When a DC constant voltage (7V) is applied to the organic EL device thus fabricated, bluish green light emission is observed. At the same luminance, the voltage of the organic EL device of Example 1 is 0.95 time of that of Comparative Example 1, 0.9 time of that of Comparative Example 2, and 0.89 time of that of Comparative Example 3. The external quantum efficiency of the organic EL device of Example 1 is 1.2 times of that of Comparative Example 1, 1.5 times of that of Comparative Example 2, and 1.2 times of that of Comparative Example 3. The luminance half-life of each of the organic electroluminescence devices thus obtained is determined by setting the device in "OLED Test System Model ST-D" manufactured by Tokyo Systems Development and driving it in a constant current mode under the condition of a forward constant current of 0.4 mA. The luminance half-life of the organic EL device of Example 1 is 1.5 times that of Comparative Example 1, 2 times that of Comparative Example 2, and 1.7 times of that of Comparative Example 3.

Example 2

In a similar manner to Comparative Example 1 except for the use of Compound (20) of the invention (emission wavelength: 445 nm) instead of Comparative Compound 1, an organic EL device of Example 2 is fabricated. When a DC constant voltage (7V) is applied to the organic EL device thus fabricated, blue light emission is observed. At the same luminance, the voltage of the organic EL device of Example 1 is 0.95 time that of Comparative Example 1, 0.9 time of that of Comparative Example 2, and 0.89 time of that of Comparative Example 3. The external quantum efficiency of the organic EL device of Example 2 is 1.1 times that of Comparative Example 1, 1.4 times that of Comparative Example 2 and 1.2 times of that of Comparative Example 3. The luminance half-life of the organic electroluminescence device thus obtained is determined by setting the device in "OLED Test System Model ST-D" manufactured by Tokyo Systems Development and driving it in a constant current mode under the condition of a forward constant current of 0.4 mA. The luminance half-life of the organic EL device of Example 2 is 1.3 times that of Comparative Example 1, 1.9 times that of Comparative Example 2 and 1.6 times of that of Comparative Example 3.

It is also possible to fabricate a luminescence device excellent in light emission performance by using another compound of the invention. The compounds of the invention can emit blue to green phosphorescence so that blue to green luminescence devices containing the compounds of the invention can be fabricated.

Examples 3 to 18

Organic EL devices of Examples 3 to 18 are fabricated in a similar manner to Comparative Example 1, except that Comparative compound (1) is replaced by the present compounds listed in the following Table 1, respectively. On the organic EL devices of Examples 3 to 18, evaluations of a driving voltage, an external quantum efficiency and a luminance half-life in the case of driving under a forward constant current of 0.4 mA are made under the same luminance condition, and data obtained by measuring their individual evaluation results against Comparative Examples 1, 2 and 3 are summarized in Table 1, Table 2 and Table 3, respectively (, wherein individual items of data are shown as relative values, with those of Comparative Examples 1, 2 and 3 each being taken as 1).

TABLE 1

Relative values based on the data obtained in Comparative Example 1

| Example No. | Light emitting material | Driving voltage | External quantum efficiency | Luminance half-life |
| --- | --- | --- | --- | --- |
| Example 3 | Compound (1) of the invention | 0.98 | 1.1 | 1.1 |
| Example 4 | Compound (19) of the invention | 0.99 | 1.1 | 1.2 |
| Example 5 | Compound (21) of the invention | 0.95 | 1.1 | 1.2 |
| Example 6 | Compound (32) of the invention | 0.98 | 1.1 | 1.3 |
| Example 7 | Compound (41) of the invention | 0.95 | 1.1 | 1.3 |
| Example 8 | Compound (42) of the invention | 0.92 | 1.2 | 1.5 |
| Example 9 | Compound (45) of the invention | 0.96 | 1.1 | 1.4 |
| Example 10 | Compound (47) of the invention | 0.91 | 1.2 | 1.3 |
| Example 11 | Compound (48) of the invention | 0.92 | 1.1 | 1.2 |
| Example 12 | Compound (49) of the invention | 0.95 | 1.2 | 1.3 |
| Example 13 | Compound (51) of the invention | 0.96 | 1.1 | 1.3 |
| Example 14 | Compound (53) of the invention | 0.93 | 1.2 | 1.4 |
| Example 15 | Compound (54) of the invention | 0.97 | 1.1 | 1.4 |
| Example 16 | Compound (55) of the invention | 0.92 | 1.2 | 1.3 |
| Example 17 | Compound (58) of the invention | 0.97 | 1.1 | 1.2 |
| Example 18 | Compound (59) of the invention | 0.96 | 1.2 | 1.3 |

TABLE 2

Relative values based on the data obtained in Comparative Example 2

| Example No. | Light emitting material | Driving voltage | External quantum efficiency | Luminance half-life |
| --- | --- | --- | --- | --- |
| Example 3 | Compound (1) of the invention | 0.94 | 1.3 | 1.5 |
| Example 4 | Compound (19) of the invention | 0.94 | 1.3 | 1.7 |
| Example 5 | Compound (21) of the invention | 0.91 | 1.3 | 1.7 |
| Example 6 | Compound (32) of the invention | 0.93 | 1.3 | 1.8 |
| Example 7 | Compound (41) of the invention | 0.90 | 1.4 | 1.9 |
| Example 8 | Compound (42) of the invention | 0.87 | 1.5 | 2.1 |
| Example 9 | Compound (45) of the invention | 0.92 | 1.4 | 1.9 |
| Example 10 | Compound (47) of the invention | 0.87 | 1.5 | 1.8 |
| Example 11 | Compound (48) of the invention | 0.88 | 1.4 | 1.7 |
| Example 12 | Compound (49) of the invention | 0.90 | 1.4 | 1.8 |
| Example 13 | Compound (51) of the invention | 0.91 | 1.4 | 1.8 |
| Example 14 | Compound (53) of the invention | 0.88 | 1.5 | 1.9 |
| Example 15 | Compound (54) of the invention | 0.92 | 1.4 | 2.0 |
| Example 16 | Compound (55) of the invention | 0.88 | 1.4 | 1.8 |
| Example 17 | Compound (58) of the invention | 0.92 | 1.4 | 1.7 |
| Example 18 | Compound (59) of the invention | 0.92 | 1.4 | 1.8 |

TABLE 3

Relative values based on the data obtained in Comparative Example 3

| Example No. | Light emitting material | Driving voltage | External quantum efficiency | Luminance half-life |
| --- | --- | --- | --- | --- |
| Example 3 | Compound (1) of the invention | 0.93 | 1.1 | 1.3 |
| Example 4 | Compound (19) of the invention | 0.93 | 1.1 | 1.4 |
| Example 5 | Compound (21) of the invention | 0.90 | 1.1 | 1.5 |

TABLE 3-continued

Relative values based on the data obtained in Comparative Example 3

| Example No. | Light emitting material | Driving voltage | External quantum efficiency | Luminance half-life |
|---|---|---|---|---|
| Example 6 | Compound (32) of the invention | 0.93 | 1.1 | 1.6 |
| Example 7 | Compound (41) of the invention | 0.90 | 1.2 | 1.6 |
| Example 8 | Compound (42) of the invention | 0.87 | 1.3 | 1.8 |
| Example 9 | Compound (45) of the invention | 0.91 | 1.2 | 1.6 |
| Example 10 | Compound (47) of the invention | 0.86 | 1.3 | 1.6 |
| Example 11 | Compound (48) of the invention | 0.87 | 1.2 | 1.4 |
| Example 12 | Compound (49) of the invention | 0.89 | 1.2 | 1.5 |
| Example 13 | Compound (51) of the invention | 0.90 | 1.2 | 1.5 |
| Example 14 | Compound (53) of the invention | 0.88 | 1.2 | 1.7 |
| Example 15 | Compound (54) of the invention | 0.91 | 1.2 | 1.7 |
| Example 16 | Compound (55) of the invention | 0.87 | 1.2 | 1.5 |
| Example 17 | Compound (58) of the invention | 0.91 | 1.2 | 1.5 |
| Example 18 | Compound (59) of the invention | 0.91 | 1.2 | 1.5 |

The platinum complex of the invention has an excellent luminescence quantum yield so that a luminescence device using the platinum complex of the invention has a high external quantum efficiency and is excellent in driving voltage, power consumption and durability.

The organic electroluminescence devices of the invention can be preferably used in the fields of display devices, displays, backlights, electrophotography, light sources for illumination, light sources for recording, light sources for exposure, light sources for reading, signs, sign boards, interiors, and optical communications. The compounds of the invention can also be used for medical applications, fluorescent brighteners, materials for photography, UV absorbing materials, laser dyes, materials for recording media, inkjet pigments, dyes for color filter, color conversion filters, and analysis.

The entire disclosure of each and every foreign patent application from which the benefit of foreign priority has been claimed in the present application is incorporated herein by reference, as if fully set forth.

What is claimed is:

1. A compound represented by the following formula (VI) or (VII):

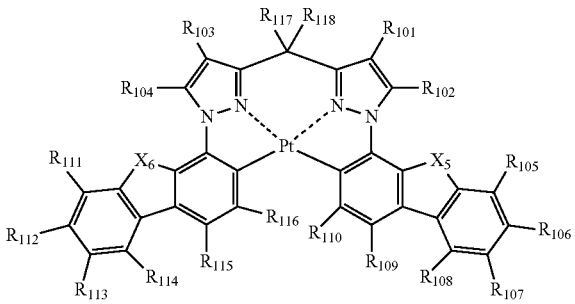

Formula (VI)

wherein each of $X_5$ and $X_6$ independently represents an oxygen atom or a sulfur atom, each of $R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $R_{115}$ and $R_{116}$ independently represents a hydrogen atom or a substituent selected from the Substituent group A, and $R_{117}$ and $R_{118}$ represent alkyl groups, cycloalkyl groups or aryl groups,

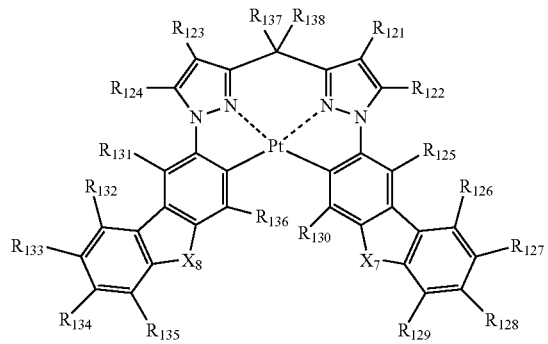

Formula (VII)

wherein each of $X_7$ and $X_8$ independently represents an oxygen atom or a sulfur atom, each of $R_{121}$, $R_{122}$, $R_{123}$, $R_{124}$, $R_{125}$, $R_{126}$, $R_{127}$, $R_{128}$, $R_{129}$, $R_{130}$, $R_{131}$, $R_{132}$, $R_{133}$, $R_{134}$, $R_{135}$ and $R_{136}$ independently represents a hydrogen atom or a substituent selected from Substituent group A, and $R_{137}$ and $R_{138}$ represent alkyl groups, cycloalkyl groups or aryl groups, wherein Substituent group A consists of an alkyl group, a cycloalkyl group, an alkenyl group, an alkenyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amide group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group, a silyl group, and a silyloxy group.

* * * * *